United States Patent
Yu et al.

(10) Patent No.: US 11,564,644 B2
(45) Date of Patent: Jan. 31, 2023

(54) SYSTEMS AND METHODS FOR X-RAY SCANNER POSITIONING

(71) Applicant: SHANGHAI UNITED IMAGING HEALTHCARE CO., LTD., Shanghai (CN)

(72) Inventors: Qianqian Yu, Shanghai (CN); Wenqiang Liu, Shanghai (CN); Bing Tang, Shanghai (CN); Shouyuan Jin, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 72 days.

(21) Appl. No.: 17/322,891

(22) Filed: May 17, 2021

(65) Prior Publication Data
US 2021/0267558 A1  Sep. 2, 2021

Related U.S. Application Data

(60) Continuation of application No. 16/866,294, filed on May 4, 2020, now Pat. No. 11,006,908, which is a (Continued)

(30) Foreign Application Priority Data

Jun. 13, 2016  (CN) .......................... 201610410580.0
Aug. 8, 2016  (CN) .......................... 201610640735.X
(Continued)

(51) Int. Cl.
*A61B 6/08* (2006.01)
*A61B 6/00* (2006.01)
*A61B 6/04* (2006.01)

(52) U.S. Cl.
CPC .............. *A61B 6/08* (2013.01); *A61B 6/0492* (2013.01); *A61B 6/547* (2013.01); *A61B 6/56* (2013.01)

(58) Field of Classification Search
CPC ...... A61B 2562/0242; A61B 2562/146; A61B 2034/107; A61B 2090/309;
(Continued)

(56) References Cited

U.S. PATENT DOCUMENTS 6,041,249 A   3/2000 Regn
9,439,619 B1  9/2016 Nance et al.
(Continued)

FOREIGN PATENT DOCUMENTS

CN   1537657 A    10/2004
CN   201847692 U  6/2011
(Continued)

OTHER PUBLICATIONS

The European Search report in European Application No. 17175783.4 dated Apr. 25, 2018, 26 pages.
(Continued)

*Primary Examiner* — Don K Wong
(74) *Attorney, Agent, or Firm* — Metis IP LLC

(57) ABSTRACT

The present disclosure relates to systems and methods for positioning an X-ray scanner. The systems may perform the methods to obtain an origin related to an X-ray scanner; determine a coordinate system based on the origin; determine coordinates of a second location of the X-ray scanner based on the origin and the coordinate system; obtain coordinates of a first location based on the origin and the coordinate system; and determine, based on the origin and the coordinates of the second location, positioning information of the X-ray scanner configured to cause the X-ray
(Continued)

scanner to be positioned at the first location from the second location of the X-ray scanner.

20 Claims, 24 Drawing Sheets

Related U.S. Application Data division of application No. 15/620,967, filed on Jun. 13, 2017, now Pat. No. 10,638,985.

(30) Foreign Application Priority Data

Aug. 11, 2016 (CN) .......................... 201610656640.7
Sep. 9, 2016 (CN) .......................... 201610816158.5

(58) Field of Classification Search
CPC ...... A61B 2090/363; A61B 2090/3937; A61B 5/0059; A61B 90/13
See application file for complete search history.

(56) References Cited

U.S. PATENT DOCUMENTS

| | | |
|---|---|---|
| 2005/0195945 A1 | 9/2005 | Gotoh |
| 2007/0036274 A1 | 2/2007 | Haras et al. |
| 2008/0192895 A1 | 8/2008 | Dehler et al. |
| 2008/0232554 A1 | 9/2008 | Heigl et al. |
| 2009/0003528 A1 | 1/2009 | Ramraj et al. |
| 2009/0251709 A1 | 10/2009 | Kindlein |
| 2009/0299218 A1 | 12/2009 | Holler et al. |
| 2010/0027742 A1 | 2/2010 | Movassaghi et al. |
| 2010/0189218 A1 | 7/2010 | Sakaguchi et al. |
| 2010/0208274 A1 | 8/2010 | Kindlein et al. |
| 2010/0329430 A1 | 12/2010 | Zeng |
| 2012/0163556 A1* | 6/2012 | Henning .............. A61N 5/1049 378/198 |
| 2013/0077745 A1 | 3/2013 | Wang et al. |
| 2014/0086382 A1 | 3/2014 | Flohr et al. |
| 2015/0003577 A1 | 1/2015 | Aulbach et al. |
| 2015/0080740 A1 | 3/2015 | Hao et al. |
| 2015/0374326 A1 | 12/2015 | Kasaoka et al. |
| 2016/0113605 A1 | 4/2016 | Bouvier et al. |
| 2016/0278732 A1 | 9/2016 | Amiri |
| 2016/0374637 A1 | 12/2016 | Lee et al. |
| 2017/0065237 A9 | 3/2017 | Bååt et al. |
| 2017/0273595 A1 | 9/2017 | Lee |

FOREIGN PATENT DOCUMENTS

| | | |
|---|---|---|
| CN | 202397483 U | 8/2012 |
| CN | 103322991 A | 9/2013 |
| CN | 203182923 U | 9/2013 |
| CN | 103494614 A | 1/2014 |
| CN | 103494614 B | 7/2015 |
| CN | 205234521 U | 5/2016 |
| CN | 107693118 A | 2/2018 |
| DE | 29710440 U1 | 8/1997 |
| DE | 102009043427 A1 | 4/2011 |
| DE | 102011005439 A1 | 9/2012 |
| EP | 2380496 B1 | 10/2017 |
| GB | 2302492 A | 1/1997 |
| JP | 2001340332 A | 12/2001 |
| JP | 2009240467 A | 10/2009 |
| JP | 2014148266 A | 8/2014 |
| JP | 2015195970 A | 11/2015 |
| WO | 2011075232 A1 | 6/2011 |
| WO | 2014148266 A1 | 9/2014 |
| WO | 2015086479 A2 | 6/2015 |

OTHER PUBLICATIONS

The Extended European Search Report in European Application No. 20173789.7 dated Jul. 17, 2020, 7 pages.

The Extended European Search Report in European Application No. 20175112.0 dated Sep. 29, 2020, 8 pages.

Notice of Reasons for Rejection in Japanese Application No. 2017-116324 dated Mar. 23, 2021, 15 pages.

* cited by examiner

1900

```
Determining a first segment between the first image target     1910
location and a first scanning location of the X-ray source of
             the X-ray scanner
```

```
Determining a second segment between the second image          1920
target location and a second scanning location of the X-ray
         source of the X-ray scanner
```

```
Determining the space target site based on the first segment   1930
             and the second segment
```

FIG. 19

SYSTEMS AND METHODS FOR X-RAY SCANNER POSITIONING

CROSS-REFERENCE TO RELATED APPLICATIONS

This application is a continuation of U.S. patent application Ser. No. 16/866,294, filed on May 4, 2020. Patent application Ser. No. 16/866,294 is a Division of U.S. patent application Ser. No. 15/620,967 (issued as U.S. Pat. No. 10,638,985) filed on Jun. 13, 2017, which claims priority of Chinese Patent Application No. 201610410580.0 filed on Jun. 13, 2016, Chinese Patent Application No. 201610640735.X filed on Aug. 8, 2016, Chinese Patent Application No. 201610656640.7 filed on Aug. 11, 2016, and Chinese Patent Application No. 201610816158.5 filed on Sep. 9, 2016, the entire contents of each of which are hereby incorporated by reference.

TECHNICAL FIELD

The present disclosure generally relates to an X-ray scanner, and more specifically relates to methods and systems for X-ray scanner positioning.

BACKGROUND

X-ray imaging is a technology that uses an X-ray scanner to scan an object to generate an X-ray image of the object. The X-ray imaging technology has been widely used in medical diagnosis, radiation therapy planning, surgery planning and other medical procedures. In existing X-ray imaging technology, there may be some problems in positioning of the X-ray scanner. For example, before a surgery, a doctor may determine an entry point on the surface of a patient. The existing X-ray scanner may include no equipment configured to indicate the entry point. A doctor may usually determine the entry point manually. Therefore, it is desirable to provide systems and methods for X-ray imaging to solve the problems in positioning of the X-ray scanner.

SUMMARY

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

According to a first aspect of the present disclosure, an X-ray scanner may comprise an X-ray source configured to emit X-rays; a detector configured to detect the X-rays that are emitted from the X-ray source, wherein the detector and the X-ray source are spaced apart by a space; an indicator configured to indicate a target position, wherein the indicator is located on a periphery of the space; and an actuator configured to actuate the indicator to perform a translation, a swing, or a combination thereof, wherein the actuator is connected with the indicator.

In some embodiments, the X-ray scanner may further comprise a support having a first end and a second end, wherein the X-ray source is connected with the first end of the support, and the detector is connected with the second end of the support.

In some embodiments, the indicator may be connected with the detector.

In some embodiments, the indicator may include a first linear laser light and a second linear laser light.

In some embodiments, the detector may include a frame having a first side and a second side connected with the first side, the first linear laser light is connected with the first side of the frame, and the second linear laser light is connected with the second side of the frame.

In some embodiments, the first linear laser light may emit first laser rays, the second linear laser light may emit second laser rays, the first linear laser light and the second linear laser light may be positioned such that the first laser rays and the second laser rays may form an intersection indicating the target position.

In some embodiments, the indicator may further include a third linear laser light and a fourth linear laser light.

In some embodiments, the third linear laser light may be connected with the first side of the frame, and the fourth linear laser light may be connected with the second side of the frame.

In some embodiments, the frame may further have a third side parallel to the first side and a fourth side parallel to the second side, the third linear laser light may be connected with the third side of the frame, and the fourth linear laser light may be connected with the fourth side of the frame.

In some embodiments, the first linear laser light may emit first laser rays, the second linear laser light may emit second laser rays, the third linear laser light may emit third laser rays, the fourth linear laser light may emit fourth laser rays, the first linear laser light, the second linear laser light, the third linear laser light, and the fourth linear laser light may be positioned such that the first laser rays, the second laser rays, the third laser rays, and the fourth laser rays may define an area indicating the target position.

In some embodiments, the actuator may include a first actuating unit and a second actuating unit, the first actuating unit may be configured to actuate the first linear laser light, and the second actuating unit may be configured to actuate the second linear laser light.

In some embodiments, the first actuating unit may include a first transmission, the first transmission may include at least one of a gear transmission, a chain transmission, or a belt transmission, and the first linear laser light may be connected with the first transmission.

In some embodiments, the first linear laser light may be connected with the first transmission through a first translation board.

In some embodiments, the indicator may include a fifth laser light, the fifth laser light may be a point laser light or a cross laser light, and the fifth laser light may be adjustable by the translation or the swing such that the fifth laser light may indicate the target position.

In some embodiments, the actuator may include a third actuating unit and a fourth actuating unit, the third actuating unit may be configured to actuate the fifth laser light to perform the translation, and the fourth actuating unit may be configured to actuate the fifth laser light to perform the swing.

In some embodiments, the third actuating unit may include a second transmission and a second translation board, and the second translation board may be connected with the second transmission.

In some embodiments, the fourth actuating unit may include a third transmission and a rotation board, the third transmission may include a gear transmission and an electric motor, the fifth laser light may be connected with the gear transmission, the gear transmission may be connected with a first side of the rotation board, the electric motor may be connected with a second side of the rotation board that is opposite to the first side of the rotation board, and the rotation board may be connected with the second translation board.

In some embodiments, the gear transmission may include a driving gear and a driven gear, and the fifth laser light may be connected with the driven gear.

In some embodiments, the driving gear may be connected with the rotation board through an axis and may be rotatable around the axis, the driven gear may be connected with the rotation board through a locating pin inserted in an opening on the driven gear such that the fifth laser light may be rotatable along the opening.

In some embodiments, the X-ray scanner may further comprise a rangefinder configured to determine a distance between the target position and the detector.

According to a second aspect of the present disclosure, a system may comprise an X-ray scanner configured to scan an object including a target; one or more processors; and one or more storage devices configured to communicate with the one or more processors. The one or more storage devices may include a set of instructions. When the one or more processors executing the set of instructions, the one or more processors may be directed to perform one or more of the following operations. The one or more processors may obtain one or more images relating to the target in the object. The one or more processors may determine one or more image target locations corresponding to the target based on the one or more images. The one or more processors may determine a target position of the target based on the one or more image target locations corresponding to the target. The one or more processors may determine positioning information of an indicator or an X-ray source of the X-ray scanner based on the target position.

According to a third aspect of the present disclosure, a method may include one or more of the following operations. The one or more processors may obtain one or more images relating to the target in the object. The one or more processors may determine one or more image target locations corresponding to the target based on the one or more images. The one or more processors may determine a target position of the target based on the one or more image target locations corresponding to the target. The one or more processors may determine positioning information of an indicator or an X-ray source of the X-ray scanner based on the target position.

In some embodiments, the determining the target position based on the one or more image target locations corresponding to the target may comprise determining a first segment between a first scanning location of the X-ray scanner and a first image target location relating to a first image, wherein the first image relates to the first scanning location of the X-ray scanner; determining a second segment between a second scanning location of the X-ray scanner and a second target location relating to a second image, wherein the second image relates to the second scanning location of the X-ray scanner; and determining the target position based on the first segment and the second segment.

In some embodiments, the determining the target position based on the first segment and the second segment may comprise determining whether there is an intersection of the first segment and the second segment; and designating, in response to a determination that there is an intersection of the first segment and the second segment, the intersection of the first segment and the second segment as the target position.

In some embodiments, the determining the target position based on the first segment and the second segment may further comprise determining, in response to a determination that there is no intersection of the first segment and the second segment, a third segment between a point in the first segment and a point in the second segment, a length of the third segment being minimum among a plurality of segments, a segment including a point in the first segment and a point in the second segment; and designating a point in the third segment as the target position.

In some embodiments, the determining the target position based on the first segment and the second segment may further comprise determining that the length of the third segment is less than or equal to a threshold.

According to a fourth aspect of the present disclosure, a system may comprise an X-ray scanner configured to scan an object; one or more processors; and one or more storage devices configured to communicate with the one or more processors. The one or more storage devices may include a set of instructions. When the one or more processors executing the set of instructions, the one or more processors may be directed to perform one or more of the following operations. The one or more processors may determine an origin of a coordinate system. The one or more processors may determine the coordinate system based on the origin. The one or more processors may determine coordinates of a current location of the X-ray scanner based on the origin and the coordinate system. The one or more processors may determine the positioning information of the X-ray scanner to be positioned at the origin from the current location of the X-ray scanner based on the origin and the coordinates of the current location.

According to a fifth aspect of the present disclosure, a method may include one or more of the following operations. The one or more processors may determine an origin of a coordinate system. The one or more processors may determine the coordinate system based on the origin. The one or more processors may determine coordinates of a current location of the X-ray scanner based on the origin and the coordinate system. The one or more processors may determine the positioning information of the X-ray scanner to be positioned at the origin from the current location of the X-ray scanner based on the origin and the coordinates of the current location.

According to a sixth aspect of the present disclosure, a non-transitory computer readable medium may comprise at least one set of instructions. The at least one set of instructions may be executed by one or more processors. The one or more processors may obtain one or more images relating to the target in the object. The one or more processors may determine one or more image target locations corresponding to the target based on the one or more images. The one or more processors may determine a target position of the target based on the one or more image target locations corresponding to the target. The one or more processors may determine positioning information of an indicator or an X-ray source of the X-ray scanner based on the target position.

According to a seventh aspect of the present disclosure, a non-transitory computer readable medium may comprise at least one set of instructions. The at least one set of instructions may be executed by one or more processors. The one or more processors may determine an origin of a coordinate system. The one or more processors may determine the coordinate system based on the origin. The one or more processors may determine coordinates of a current location of the X-ray scanner based on the origin and the coordinate system. The one or more processors may determine the positioning information of the X-ray scanner to be positioned at the origin from the current location of the X-ray scanner based on the origin and the coordinates of the current location.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

FIG. 19 is a flowchart illustrating an exemplary process for determining a target position of a target according to some embodiments of the present disclosure;

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, section or assembly of different level in ascending order.

However, the terms may be displaced by other expression if they achieve the same purpose.

Figure 7:
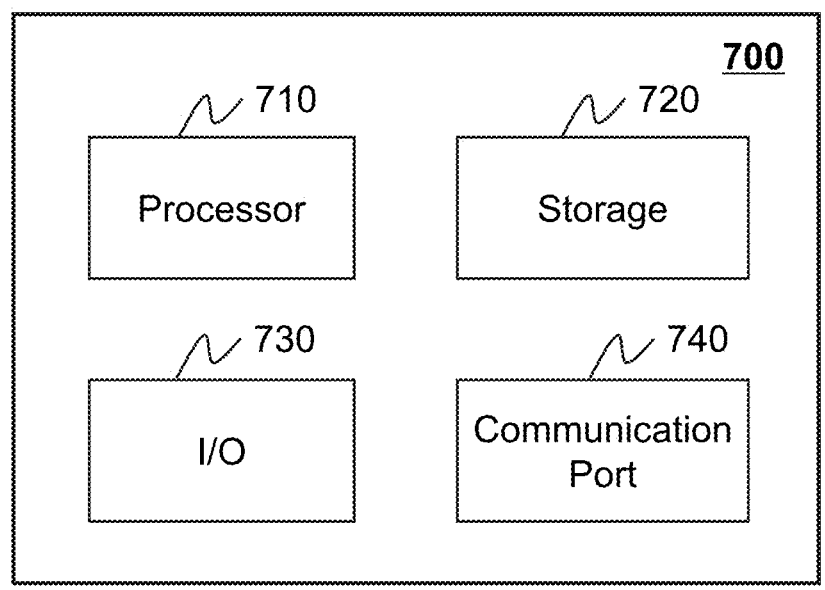
FIG. 7 is a schematic diagram illustrating exemplary hardware and/or software components of an exemplary computing device on which a processing engine may be implemented according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or other storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., the processor 710 as illustrated in FIG. 7) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in a firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

Provided herein are systems and components for medical imaging. In some embodiments, the imaging system may include a single modality imaging system and/or a multi-modality imaging system. The single modality imaging system may include, for example, an X-ray scanner positioning system, an emission computed tomography (ECT) system, a magnetic resonance imaging (MRI) system, an ultrasonography system, a positron emission tomography (PET) system, or the like, or any combination thereof. The multi-modality imaging system may include, for example, a X-ray imaging-magnetic resonance imaging (X-ray-MRI) system, a positron emission tomography-X-ray imaging (PET-X-ray) system, a single photon emission computed tomography-magnetic resonance imaging (SPECT-MRI) system, a digital subtraction angiography-magnetic resonance imaging (DSA-MRI) system, etc.

For illustration purposes, the disclosure describes systems and methods relating to X-ray scanner. It should be noted that the X-ray scanner positioning system 100 described below is merely provided for illustration purposes, and not intended to limit the scope of the present disclosure.

Figure 1:
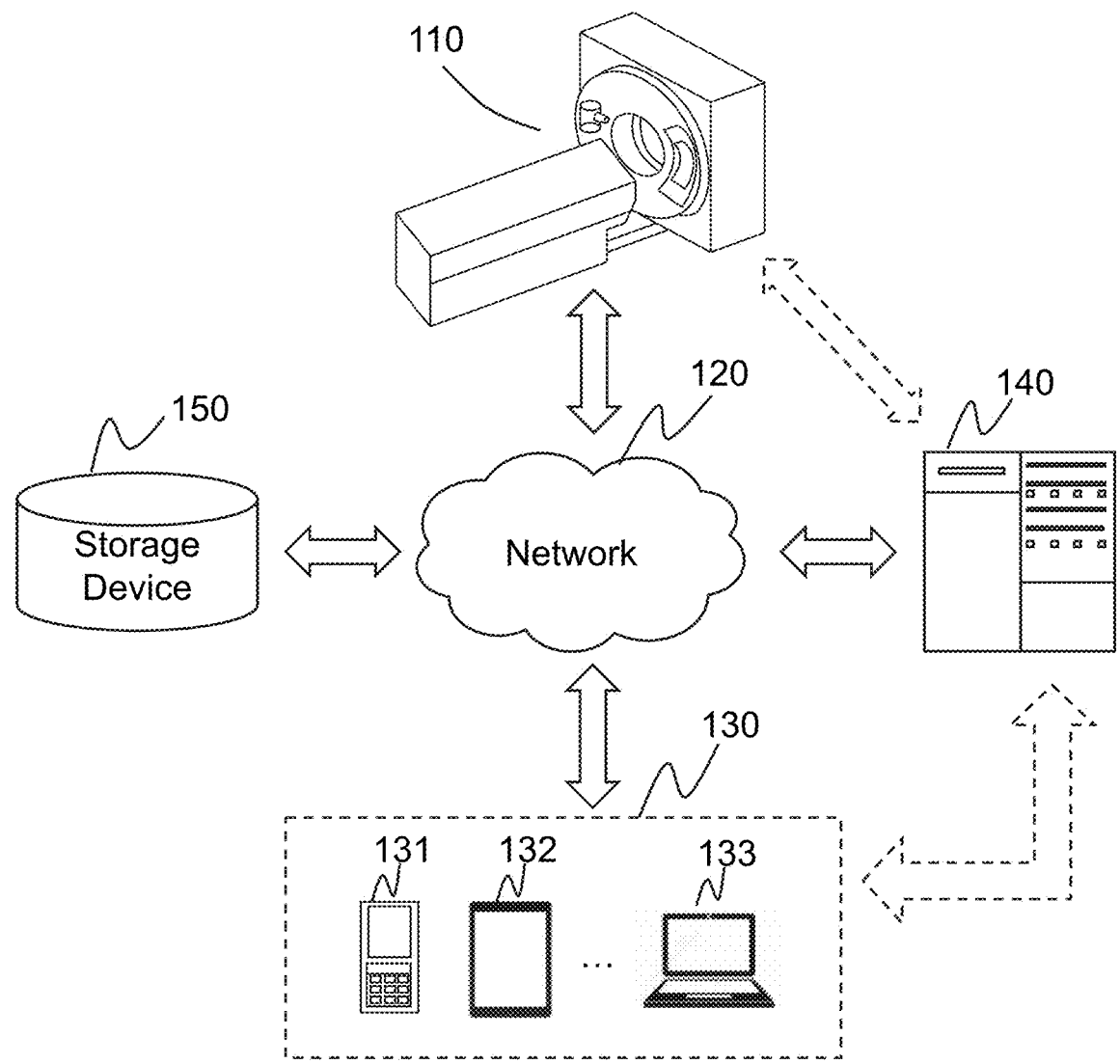
FIG. 1 is a schematic diagram illustrating an exemplary X-ray scanner positioning system according to some embodiments of the present disclosure.

FIG. 1 is a schematic diagram illustrating an exemplary X-ray scanner positioning system 100 according to some embodiments of the present disclosure. As shown in FIG. 1, the X-ray scanner positioning system 100 may include an X-ray scanner 110, a network 120, one or more terminals 130, a processing engine 140, and a storage device 150. The connection between the components in the X-ray scanner positioning system 100 may be variable. For example, the X-ray scanner 110 and/or the terminal(s) 130 may be connected to the processing engine 140 through the network 120. As another example, the X-ray scanner 110 and/or the terminal(s) 130 may be connected to the processing engine 140 directly.

The X-ray scanner 110 may be configured to scan an object using X-rays and generate imaging data used to generate one or more images relating to the object. In some embodiments, the X-ray scanner 110 may transmit the imaging data to the processing engine 140 for further processing (e.g., generating one or more images). In some embodiments, the imaging data and/or the one or more images associated with the object may be stored in the storage device 150 and/or the processing engine 140.

In some embodiments, the X-ray scanner 110 may include a C-arm X-ray scanner, a computed tomography (CT) scanner, a digital radiography (DR) scanner, a digital substraction angiography (DSA) scanner, a dynamic spatial reconstructor (DSR) scanner, an X-ray microscopy scanner, a multi-modality scanner, or the like, or a combination thereof. Exemplary multi-modality scanners may include a computed tomography-positron emission tomography (CT-PET) scanner, a computed tomography-magnetic resonance imaging (CT-MRI) scanner, etc. The object may be biological or non-biological. Merely by way of example, the object may include a patient, a man-made object, etc. As another example, the object may include a specific portion, organ, and/or tissue of a patient. For example, the object may include head, brain, neck, body, shoulder, arm, thorax, cardiac, stomach, blood vessel, soft tissue, knee, feet, or the like, or any combination thereof.

The network 120 may include any suitable network that can facilitate exchange of information and/or data for the X-ray scanner positioning system 100. In some embodiments, one or more components of the X-ray scanner positioning system 100 (e.g., the X-ray scanner 110, the terminal(s) 130, the processing engine 140, the storage device 150, etc.) may communicate information and/or data with one or more other components of the X-ray scanner positioning system 100 via the network 120. For example, the processing engine 140 may obtain image data from the X-ray scanner 110 via the network 120. As another example, the processing engine 140 may obtain user instructions from the terminal(s) 130 via the network 120. The network 120 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network (VPN), a satellite network, a telephone network, routers, hubs, witches, server computers, and/or any combination thereof. Merely by way of example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired and/or wireless network access points such as base stations and/or internet exchange points through which one or more components of the X-ray scanner positioning system 100 may be connected to the network 120 to exchange data and/or information.

The terminal(s) 130 may include a mobile device 131, a tablet computer 132, a laptop computer 133, or the like, or any combination thereof. In some embodiments, the mobile device 131 may include a smart home device, a wearable device, a mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, a footgear, eyeglasses, a helmet, a watch, clothing, a backpack, a smart accessory, or the like, or any combination thereof. In some embodiments, the mobile device may include a mobile phone, a personal digital assistance (PDA), a gaming device, a navigation device, a point of sale (POS) device, a laptop, a tablet computer, a desktop, a virtual reality device, or the like, or any combination thereof. In some embodiments, the virtual reality device and/or the augmented reality device may include a virtual reality helmet, virtual reality glasses, a virtual reality patch, an augmented reality helmet, augmented reality glasses, an augmented reality patch, or the like, or any combination thereof. For example, the virtual reality device and/or the augmented reality device may include a Google Glass™, an Oculus Rift™, a Hololens™, a Gear VR™, etc. In some embodiments, the terminal(s) 130 may be part of the processing engine 140.

The processing engine 140 may process data and/or information obtained from the X-ray scanner 110, the terminal(s) 130, and/or the storage device 150. For example, the processing engine 140 may process imaging data generated by the X-ray scanner 110 to generate an image. As another example, the processing engine 140 may determine positioning information of the X-ray scanner 110. In some embodiments, the processing engine 140 may be a single server or a server group. The server group may be centralized or distributed. In some embodiments, the processing engine 140 may be local or remote. For example, the processing engine 140 may access information and/or data stored in the X-ray scanner 110, the terminal(s) 130, and/or the storage device 150 via the network 120. As another example, the processing engine 140 may be directly connected to the X-ray scanner 110, the terminal(s) 130 and/or the storage device 150 to access stored information and/or data. In some embodiments, the processing engine 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing engine 140 may be implemented by a computing device 700 having one or more components as illustrated in FIG. 7.

The storage device 150 may store data, instructions, and/or any other information. In some embodiments, the storage device 150 may store data obtained from the terminal(s) 130 and/or the processing engine 140. In some embodiments, the storage device 150 may store data and/or instructions that the processing engine 140 may execute or use to perform exemplary methods described in the present disclosure. In some embodiments, the storage device 150 may include a mass storage, a removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 150 may be connected to the network 120 to communicate with one or more other components in the X-ray scanner positioning system 100 (e.g., the processing engine 140, the terminal(s) 130, etc.). One or more components in the X-ray scanner positioning system 100 may access the data or instructions stored in the storage device 150 via the network 120. In some embodiments, the storage device 150 may be directly connected to or communicate with one or more other components in the X-ray scanner positioning system 100 (e.g., the processing engine 140, the terminal(s) 130, etc.). In some embodiments, the storage device 150 may be part of the processing engine 140.

This description is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. For example, the storage device 150 may be a data storage including cloud computing platforms, such as, a public cloud, a private cloud, a community and hybrid cloud, etc. As another example, the processing engine 140 and the X-ray scanner 110 may be integrated into one single device. However, those variations and modifications do not depart the scope of the present disclosure.

Figure 2A:
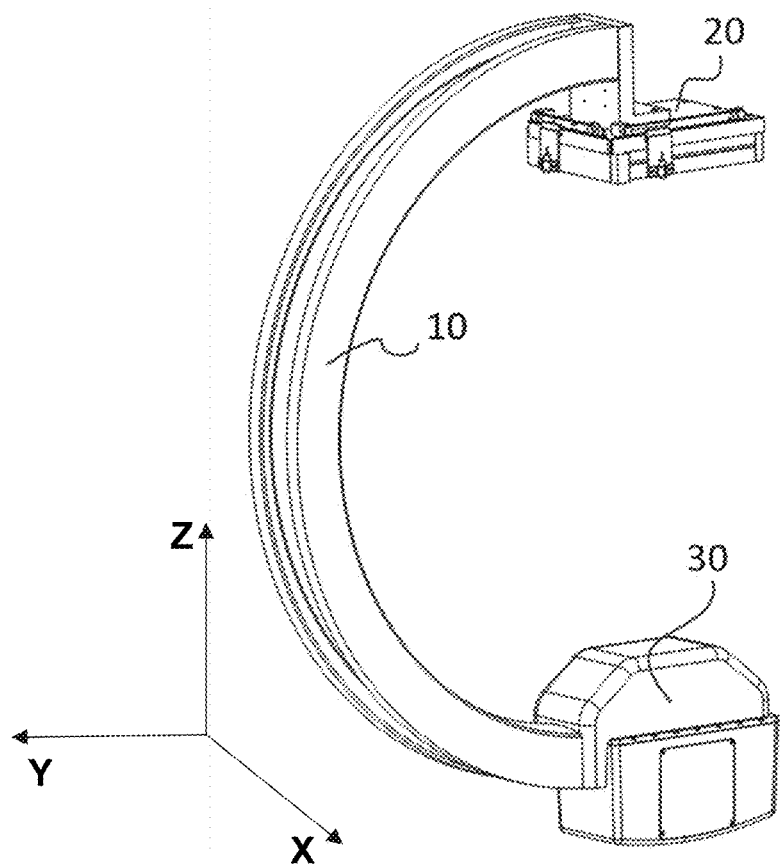
FIG. 2A is a schematic diagram illustrating an exemplary X-ray scanner according to some embodiments of the present disclosure.

FIG. 2A is a schematic diagram illustrating an exemplary X-ray scanner 110 according to some embodiments of the present disclosure. As shown in FIG. 2A, the X-ray scanner 110 may include a support 10, a detector 20, and an X-ray source 30. The support 10 may be configured to support the X-ray source 30 and the detector 20. In some embodiments, the support 10 may have an O-shape, a U-shape, a G-shape, a C-shape, or the like, or a combination thereof. In some embodiments, the X-ray source 30 and the detector 20 may be connected with the support 10. For example, the support 10 of a C-shape, a U-shape, a G-shape, etc., may have a first end and a second end. The first end may be connected to the X-ray source 30, and the second end may be connected to the detector 20. As another example, for the support 10 of an O-shape, the X-ray source 30 and the X-ray source 30 may be attached to the support 10, and spaced from each other. For instance, the detector 20 may be opposite to the X-ray source 30, and a line linking the detector 20 and the X-ray source 30 may pass through the center of the O-shape. In some embodiments, the detector 20 and the X-ray source 30 may be spaced apart by a space. The space may be configured to accommodate an object. In some embodiments, the detector 20 and the X-ray source 30 may move with the support 10. For example, the detector 20 and the X-ray source 30 may translate with the support 10 using a moveable device (e.g., a trolley, or wheels) mounted on the X-ray scanner 110. As another example, the detector 20 and the X-ray source 30 may rotate with the support 10 along an axis that passes through the center of the support 10 and is parallel to the X axis in FIG. 2A. As still another example, the detector 20 and the X-ray source 30 may rotate with the support 10 along an axis that passes through the center of the support 10 and is parallel to the Z axis in FIG. 2A. As still another example, the detector 20 and the X-ray source 30 may rotate with the support 10 along an axis that passes through the center of the support 10 and is parallel to the Y axis in FIG. 2A. In some embodiments, while the detector 20 and the X-ray source 30 move with the support 10, the position of the detector 20 may remain the same relative to the position of the X-ray source 30. In some embodiments, the X-ray source 30 may move relative to the detector 20. For instance, the X-ray source 30 may rotate relative to the detector 20, while the position of the X-ray source 30 remains the same relative to position of the detector 20.

The X-ray source 30 may emit one or more X-rays traveling toward the object. In some embodiments, the X-ray source 30 may include a tube, such as a cold cathode ion tube, a high vacuum hot cathode tube, a rotating anode tube, etc. The tube may be powered by a high voltage generator, emitting X-rays that may be detected by the detector 20. The X-rays emitted by the X-ray source 30 may be guided to form a beam having the shape of a line, a narrow pencil, a narrow fan, a fan, a cone, a wedge, an irregular shape, or the like, or a combination thereof.

The detector 20 may detect X-rays emitted from the X-ray source 30. In some embodiments, the detector 20 may convert the detected X-rays into electric signals. The detector 20 may include one or more detector units positioned to form a structure including a plurality of pixels and/or channels. For instance, the detector units positioned to form an arcuate structure. The pixels and/or channels may be arranged in a single row, two rows, or another number of rows. The pixels and/or channels may detect the X-rays to generate electric signals. For example, a pixel and/or channel may include a scintillator layer that may absorb X-rays, and emit a visible light that can be detected by a photodiode. The photodiode may convert the visible light into an electrical signal. In some embodiments, the detected X-rays may be converted directly into an electrical signal by a suitable direct conversion material, such as amorphous selenium. An analog/digital converter in the X-ray scanner 110 may convert the electric signals into digital signals that may be referred to as imaging data. The detector 20 may have any suitable shape. For example, the detector 20 may have the shape of an arc, a circle, a rectangle, or the like, or a combination thereof. In some embodiments, the detector 20 may be and/or include a film-based detector.

The X-ray scanner 110 may include a portable X-ray scanner, a suspension X-ray scanner, a floor X-ray scanner, etc. The portable X-ray scanner may refer to an X-ray scanner that is movable on the ground. In some embodiments, the portable X-ray scanner may be mounted on a moveable device (e.g., a trolley, or wheels). The portable X-ray scanner may be moved by moving the movable device manually or by a driving device (e.g., a vehicle). The suspension X-ray scanner may refer to an X-ray scanner that is connected to a guide rail mounted on, for example, a ceiling, and the suspension X-ray scanner may be moved along the guide rail driven manually or by a driving device. The floor X-ray scanner may refer to an X-ray scanner that is fixed on, for example, a bracket on the floor, or fixed on the floor directly.

In some embodiments, the X-ray scanner 110 may further include one or more rangefinders configured to determine a distance between two points. For example, a rangefinder may determine a distance between the object and the detector 20. In some embodiments, the rangefinder(s) may be connected with the detector 20 and/or the X-ray source 30. In some embodiments, a rangefinder may include one or more sensors, for example, a placement sensor, a speed sensor, an accelerometer, or the like, or a combination thereof.

This description is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. However, those variations and modifications do not depart the scope of the present disclosure. For example, the X-ray scanner 110 may include one or more connectors and/or fixing members configured to connect the detector 20 and/or the X-ray source 30 with the support 10.

In some embodiments, the X-ray scanner 110 may further include an indicating apparatus. The indicating apparatus may include an indicator and an actuator. The indicator may be configured to indicate a location (e.g., a location on the surface of an object, or the target position of a target described in FIGS. 11-15). In some embodiments, the indicator may be located on the support 10 directly or a periphery of the space between the X-ray source 30 and the detector 20. In some embodiments, the indicator may be mounted on the upper end of the support 10 directly or the detector 20 (or the X-ray source 30). For example, if the detector 20 is located at the upper of the support 10, the indicator may be mounted on the detector 20. If the X-ray source 30 is located at the upper of the support 10, the indicator may be mounted on the X-ray source 30. In some embodiments, the indicator may include one or more laser lights.

The actuator may be configured to actuate the indicator to undergo a translation and/or a swing. The actuator may be connected with the indicator. In some embodiments, the actuator may actuate the indicator through one or more gears, one or more belts, one or more chains, or the like, or a combination thereof.

Figure 2B:
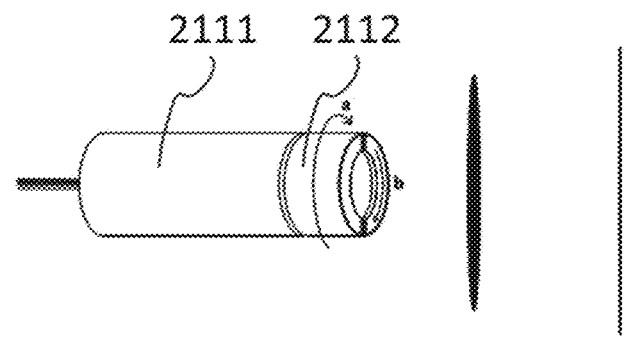
FIG. 2B is a schematic diagram illustrating an exemplary laser light according to some embodiments of the present disclosure.

FIG. 2B is a schematic diagram illustrating an exemplary laser light according to some embodiments of the present disclosure. As shown, the laser light may include a laser source 2111 and a light modulator 2112. The laser source 2111 may emit one or more laser rays. The laser source 2111 may include a solid laser source, a gas laser source, a semiconductor laser source, a liquid laser source, or the like, or a combination thereof. The light modulator 2112 may be configured to adjust one or more parameters of the laser rays, such as a shape, a color, a brightness, etc. For example, the light modulator 2112 may be configured with one or more holes of various shapes, such as circle, cross, rectangle, etc. The light modulator 2112 may be rotatable (e.g., the light modulator 2112 may rotate along a direction from "a" to "b" as shown in FIG. 2B) such that laser rays emitted from the laser source 2111 may be emitted from a hole of a specific shape. In some embodiments, the laser light may include a linear laser light, a point laser light, a cross laser light, etc.

Figure 3A:
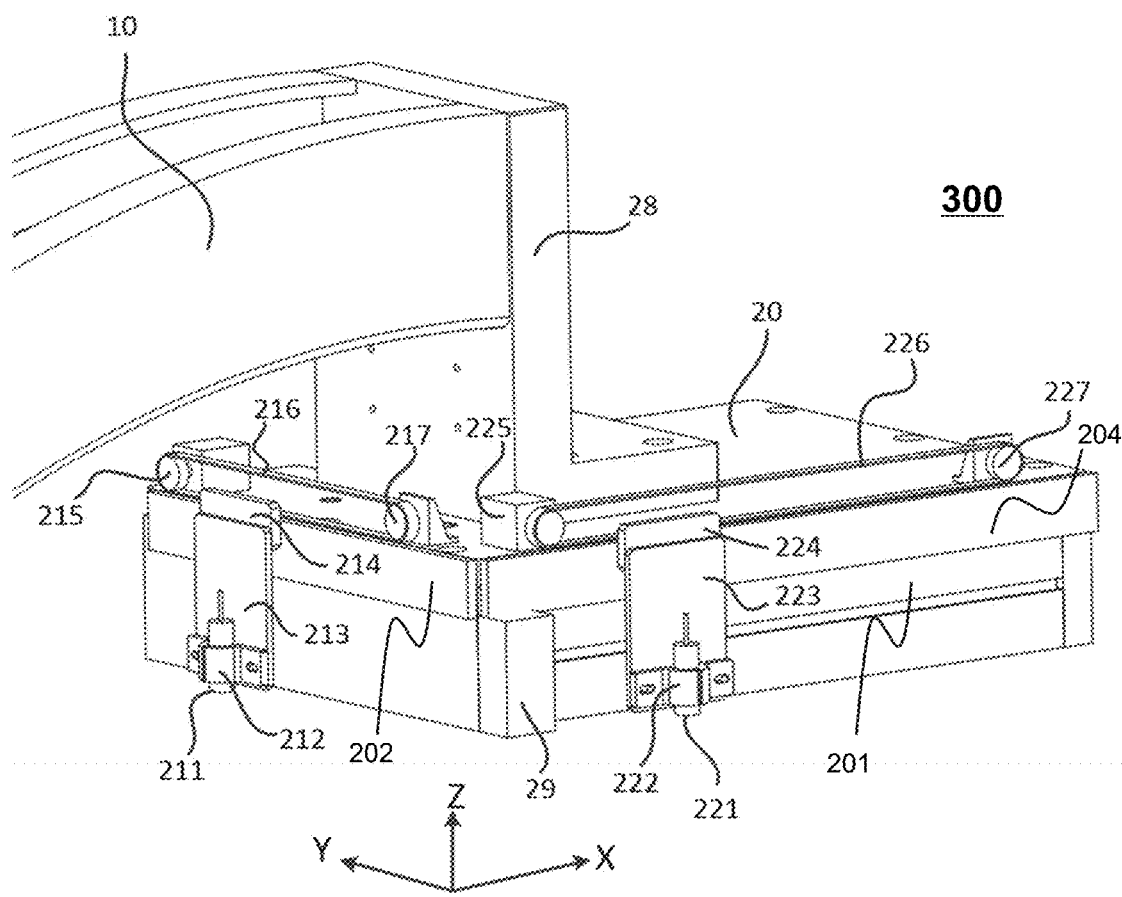
FIG. 3A is a schematic diagram illustrating an exemplary indicating apparatus according to some embodiments of the present disclosure.

FIG. 3A is a schematic diagram illustrating an exemplary indicating apparatus 300 according to some embodiments of the present disclosure. As shown in FIG. 3A, the indicator may be mounted on the detector 20. The detector 20 may be connected with the support 10 by a connector 28. The connector 28 may be of an L-shape. The detector 20 may include a frame 201 including a first side 202 and a second side 204 adjoining the first side 202. In some embodiments, the frame illustrated in FIG. 3A may include a right-angle frame, a rectangle frame, etc.

The indicator of the indicating apparatus 300 may include two laser lights, a first laser light 211 and a second laser light 221. The first laser light 211 and the second laser light 221 may be linear laser lights. In some embodiments, the first laser light 211 may be mounted on the first side 202 of the frame 201 and the second laser light 221 may be mounted on the second side 204 of the frame 201. The first laser light 211 may emit first laser rays parallel to the second side 204 of the frame 201 (also indicate by the X-axis direction as shown in FIG. 3A) and the second laser light 221 may emit second laser rays parallel to the first side 202 of the frame 201 (also indicated by the Y-axis direction as shown in FIG. 3A). In some embodiments, the first laser light 211 and the second laser light 221 may be positioned such that the first laser rays and the second laser rays may form an intersection indicating a location (e.g., the target position of a target that is descried in detail in connection with FIGS. 11-13).

Figure 3B:
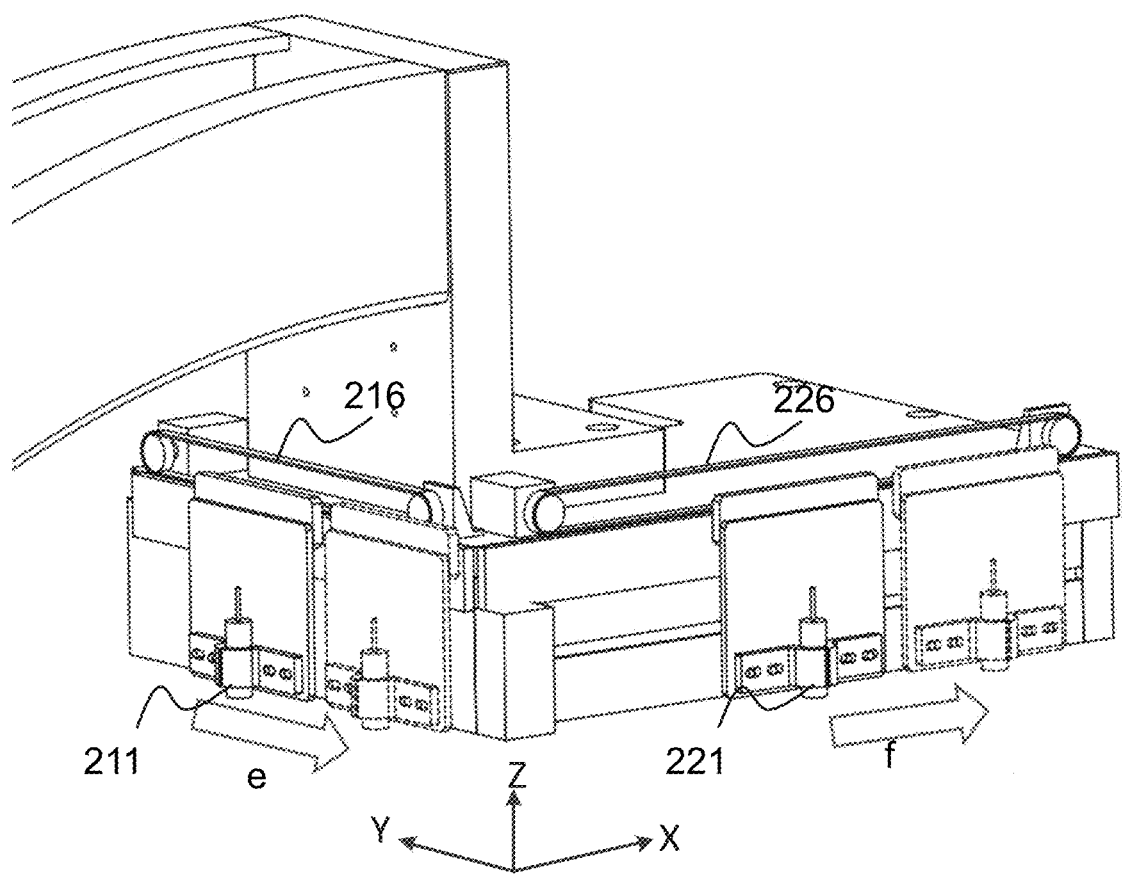
FIG. 3B is a schematic diagram illustrating an exemplary process for actuating an indicator according to some embodiments of the present disclosure.

The actuator of the indicating apparatus 300 may include a first actuating unit and a second actuating unit. The first laser light 211 may be driven by the first actuating unit and the second laser light 211 may be driven by the second actuating unit. For example, as shown in FIG. 3B, the first actuating unit may actuate the first laser light 211 to perform a translation along the first side of the frame (also indicated as the Y-axis direction). The second actuating unit may actuate the second laser light 221 to perform a translation along the second side of the frame (also indicated as the X-axis direction).

For illustration purposes, the first actuating unit may be described as an example. The first laser light 211 may be connected with the first actuating unit. The first actuation unit may include a first transmission. The first transmission may include a gear transmission, a chain transmission, a belt transmission, or the like, or a combination thereof. For illustration purposes, the belt transmission may be described as an example. The belt transmission may include a driving wheel 215, a belt 216, and a driven wheel 217. The belt 216 may connect the driving wheel 215 with the driven wheel 217. The driven wheel 217 may rotate driven by the driving wheel 215 via the belt 216. The second transmission may be similar to the first transmission. As illustrated in FIG. 3A, the components 225, 226, and 227 of the second transmission are similar to the components of 215, 216, and 217 of the first transmission.

The first laser light 211 may be connected with the belt 216 such that the first laser light 211 may translate with the belt 216. In some embodiments, the first laser light 211 may be mounted on a first translation board 213 by a connector, such as a screw, a rivet, a pin, etc. Further, the first laser light 211 may be mounted on the first translation board 213 through a fixing member 212. The fixing member 212 may be connected with the first translation board 213 by a connector, such as a screw, a rivet, a pin, etc. The first translation board 213 may be connected with the belt 216. Further, the first translation board 213 may be connected with the belt 216 through a first bearing plate 214. The first bearing plate 214 may be configured to adjust a distance between the first translation board 213 and the belt 216. In some embodiments, the second actuating unit may be same as or different to the first actuating unit. In some embodiments, the connection method between the second actuating unit and the second laser light may be same as or different to the connection method between the first actuating unit and the first d laser light.

In some embodiments, a rangefinder 29 may be mounted on the detector 20.

FIG. 3B is similar to FIG. 3A. As illustrated in FIG. 3B, the first laser light 211 may translate forward and backward along the direction of the Y axis as illustrated by the arrow e, and the second laser light 221 may translate forward and backward along the direction of the X axis as illustrated by the arrow f.

Figure 4:
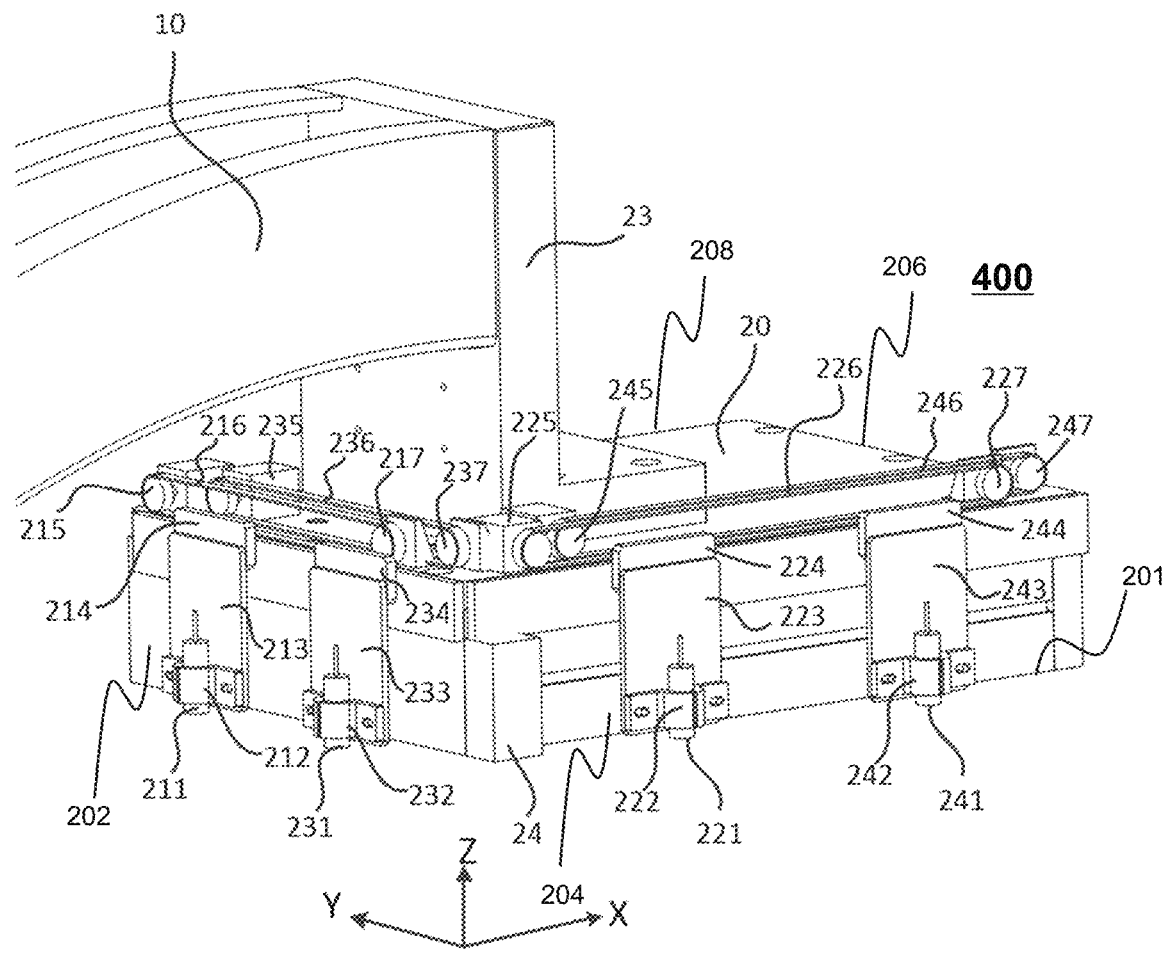
FIG. 4 is a schematic diagram illustrating an exemplary indicating apparatus according to some embodiments of the present disclosure.

FIG. 4 is a schematic diagram illustrating an exemplary indicating apparatus 400 according to some embodiments of the present disclosure. As shown in FIG. 4, a difference between the indicator of the indicating apparatus 400 and the indicator of the indicating apparatus 300 is that the indicator of the indicating apparatus 400 may further include a third laser light 231 and a fourth laser light 241. In some embodiments, the third laser light 231 and the fourth laser light 241 may be linear laser lights. In some embodiments, the third laser light 231 may be mounted on the first side 202 of the frame 201 of the detector 20 and the fourth laser light 241 may be mounted on the second side 204 of the frame 201 of the detector 20.

In some embodiments, the frame 201 (e.g., a rectangle frame) may further include a third side 206 parallel to the first side 202 and a fourth side 208 parallel to the second side 204. The third laser light 231 may be mounted on the third side 206 of the frame of the detector 20 and the fourth laser light 241 may be mounted on the fourth side 208 of the frame of the detector 20.

The third laser light 231 may emit third laser rays parallel to the second side 204 of the frame 201 (also indicated by the X-axis direction as shown in FIG. 4) and the fourth laser light 241 may emit fourth laser rays parallel to the first side 202 of the frame 201 (also indicated by the Y-axis direction as shown in FIG. 4). In some embodiments, the first laser light 211, the second laser light 221, the third laser light 231, and the fourth laser light 241 may be positioned such that the first laser rays, the second laser rays, the third laser rays, and the fourth laser rays may define an area indicating a location (e.g., the target position of a target that is descried in detail in connection with FIG. 11 and/or FIG. 14).

In some embodiments, a difference between the actuator of the indicating apparatus 400 and the actuator of the indicating apparatus 300 is that the actuator of the indicating apparatus 400 may further include a third actuating unit and a fourth actuating unit. The third actuating unit may actuate the third laser light 231 to perform a translation along the Y-axis direction illustrated in FIG. 4. The fourth actuating unit may actuate the fourth laser light 241 to perform a translation along the X-axis direction illustrated in FIG. 4.

In some embodiments, the third actuating unit (or the fourth actuating unit) may be same as or different to the first actuating unit. The third actuating unit may include a third transmission. The third transmission may be similar to the first transmission. As illustrated in FIG. 4, the components 235, 236, and 237 of the third transmission are similar to the components of 215, 216, and 217 of the first transmission. The fourth actuating unit may include a fourth transmission. The fourth transmission may be similar to the first transmission. As illustrated in FIG. 4, the components 245, 246, and 247 of the third transmission are similar to the components of 215, 216, and 217 of the first transmission.

In some embodiments, the connection method between the third actuating unit (or the fourth actuating unit) and the third laser light (or the fourth laser light) may be same as or different to the connection method between the first actuating unit and the first laser light.

Figure 5A:
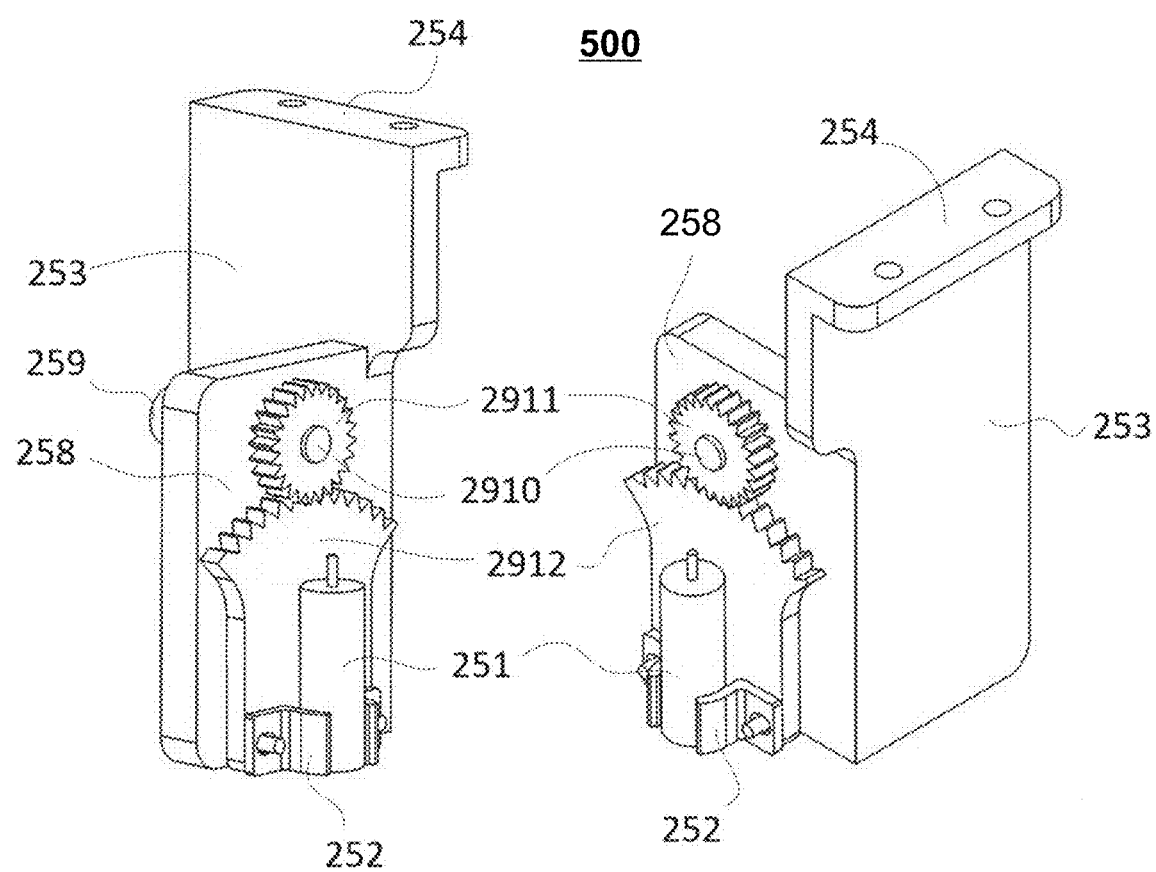
FIG. 5A is schematic diagram illustrating perspective views of an exemplary indicating apparatus according to some embodiments of the present disclosure.
Figure 5B:
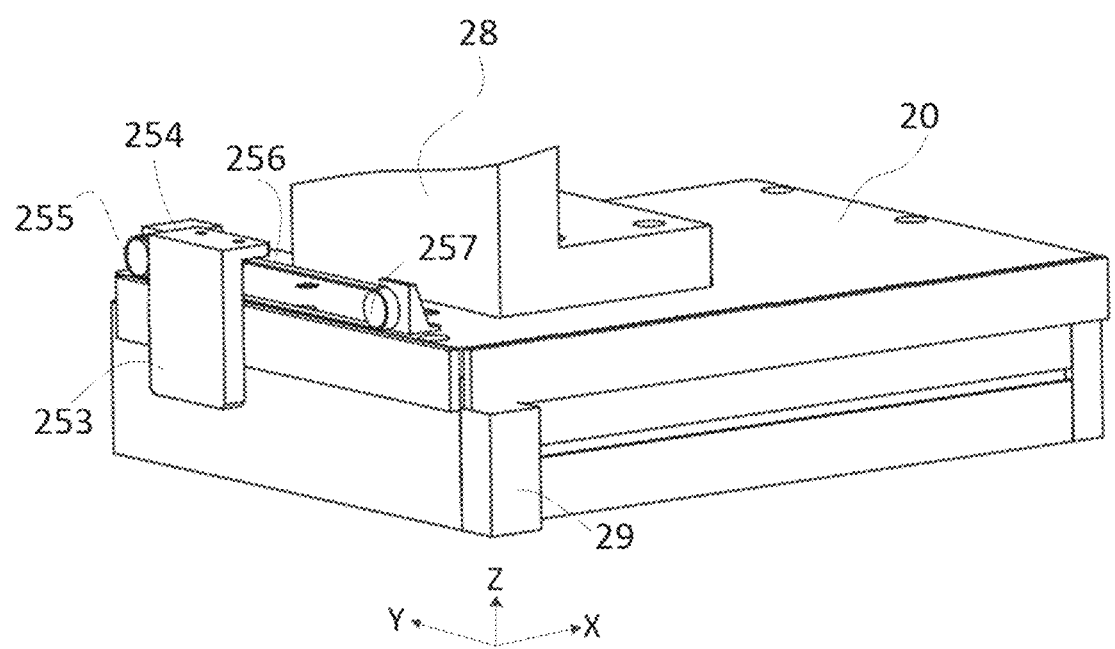
FIG. 5B is a schematic diagram illustrating an exemplary detector according to some embodiments of the present disclosure.

FIGS. 5A-5B are schematic diagrams illustrating three perspective views of an exemplary indicating apparatus 500 according to some embodiments of the present disclosure. As shown in FIG. 5A, the indicator of the indicating apparatus 500 may include a fifth laser light 251. The fifth laser light 251 may include a cross laser light, a point laser light, etc.

In some embodiments, the actuator of the indicating apparatus 500 may include a fifth actuating unit configured to actuate the fifth laser light 251 to move along a first direction, and a sixth actuating unit configured to actuate the fifth laser light 251 to move along a second direction. For example, the fifth actuating unit may actuate the fifth laser light 251 to perform a translation. The sixth actuating unit may actuate the fifth laser light 251 to perform a swing. The fifth actuating unit may be connected with the sixth actuating unit.

The fifth actuating unit may include a fifth transmission and a second translation board 253. The fifth transmission may include a gear transmission, a chain transmission, a belt transmission, or the like, or a combination thereof. For illustration purposes, the fifth transmission may be similar to the first transmission. As illustrated in FIG. 5B, the components 255, 256, and 257 of the fifth transmission are similar to the components of 215, 216, and 217 of the first transmission. The second translation board 253 may be connected with the fifth transmission. Further, the second translation board 253 may be connected with the fifth transmission through a second bearing plate 254. The second bearing plate 254 may be configured to adjust a distance between the second translation board 253 and the fifth transmission.

The sixth actuating unit may include a sixth transmission and a rotation board 258. The sixth transmission may include an electric motor 259 and a gear transmission. The fifth laser light 251 may be connected with the gear transmission. The gear transmission may be connected with a first side of the rotation board 258, and the electric motor 259 may be connected with a second side of the rotation board 258 that is opposite to the first side of the rotation board 258. The rotation board 258 may be connected with the second translation board 253.

The gear transmission may include a driving rod 2910, a driving gear 2911, and a driven gear 2912. The electric motor 259 may be configured to actuate the driving rod 2910 to rotate. The driving rod 2910 may pass through the rotation board 258 and the driving gear 2911, and be connected with the electric motor 259. The driving gear 2911 may be actuated to rotate by the driving rod 2910. The driven gear 2912 may be coupled with the driving gear 2911 such that the driven gear 2912 may be actuated to rotate by the driving gear 2911. In some embodiments, the driven gear 2912 may be configured to be in various shapes, for example, circular, flabellate, etc.

The fifth laser light 251 may be mounted on the driven gear 2912. In some embodiments, the fifth laser light 251 may be coupled to driven gear 2912 through a fixing member 252. The fixing member 252 may be a one-piece structure, or a multi-piece structure (e.g., a two-piece structure as illustrated in FIG. 5A). The fixing member 252 may be connected with the driven gear 2912 by a connector, such as a screw, a rivet, a pin, or the like, or a combination thereof. In some embodiments, the fifth laser light 251 may swing with the driven gear 2912.

For the purposes of illustration, the indicating apparatus 500 may be mounted on one side of the detector 20 (e.g., one side parallel to the Y axis shown in FIG. 5B). The fifth actuating unit may actuate the fifth laser light 251 to translate along the Y-axis direction shown in FIG. 5B. The sixth actuating unit may actuate the fifth laser light 251 to swing about the Z-axis direction shown in FIG. 5B.

Figure 6:
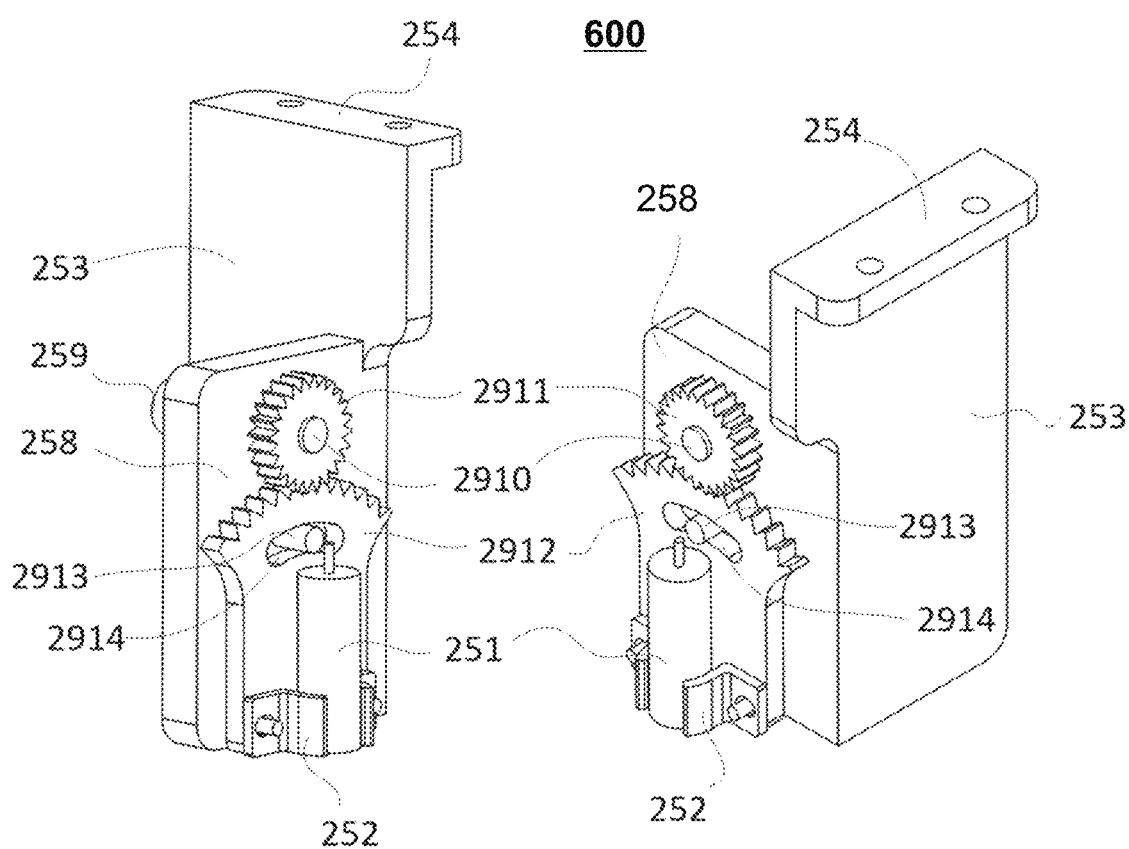
FIG. 6 is a schematic diagram illustrating an exemplary indicating apparatus according to some embodiments of the present disclosure.

FIG. 6 is a schematic diagram illustrating an exemplary indicating apparatus 600 according to some embodiments of the present disclosure. The indicating apparatus 600 illustrated in FIG. 6 is similar to the indicating apparatus 500 as illustrated in FIG. 5A and FIG. 5B except for a few features. As shown in FIG. 6, the gear transmission of the sixth actuating unit may further include a locating pin 2913. The locating pin 2913 may be mounted on the rotation board 258. The locating pin 2913 may be inserted in an opening 2914 on the driven gear 2912. In some embodiments, the opening 2914 may be configured in, for example, an arc shape. The opening 2914 may be configured to define a swing path of the driven gear 2912 such that the fifth laser light may swing along the opening.

FIG. 7 is a schematic diagram illustrating exemplary hardware and/or software components of an exemplary computing device 700 on which the processing engine 140 may be implemented according to some embodiments of the present disclosure. As illustrated in FIG. 7, the computing device 700 may include a processor 710, a storage 720, an input/output (I/O) 730, and a communication port 740.

The processor 710 may execute computer instructions (e.g., program code) and perform functions of the processing engine 140 in accordance with techniques described herein. The computer instructions may include, for example, routines, programs, objects, components, data structures, procedures, modules, and functions, which perform particular functions described herein. For example, the processor 710 may process imaging data obtained from the X-ray scanner 110, the terminal(s) 130, the storage device 150, and/or any other component of the X-ray scanner positioning system 100. In some embodiments, the processor 710 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 700. However, it should be noted that the computing device 700 in the present disclosure may also include multiple processors, thus operations and/or method steps that are performed by one processor as described in the present disclosure may also be jointly or separately performed by the multiple processors. For example, if in the present disclosure the processor of the computing device 700 executes both operation A and operation B, it should be understood that operation A and operation B may also be performed by two or more different processors jointly or separately in the computing device 700 (e.g., a first processor executes operation A and a second processor executes operation B, or the first and second processors jointly execute operations A and B).

The storage 720 may store data/information obtained from the X-ray scanner 110, the terminal(s) 130, the storage device 150, and/or any other component of the X-ray scanner positioning system 100. In some embodiments, the storage 720 may include a mass storage, a removable storage, a volatile read-and-write memory, a read-only memory (ROM), or the like, or any combination thereof. For example, the mass storage may include a magnetic disk, an optical disk, a solid-state drives, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage 720 may store one or more programs and/or instructions to perform exemplary methods described in the present disclosure. For example, the storage 720 may store a program for the processing engine 140 for determining positioning information of the X-ray scanner 110.

The I/O 730 may input and/or output signals, data, information, etc. In some embodiments, the I/O 730 may allow a user interaction with the processing engine 140. In some embodiments, the I/O 730 may include an input device and an output device. Examples of the input device may include a keyboard, a mouse, a touch screen, a microphone, or the like, or a combination thereof. Examples of the output device may include a display device, a loudspeaker, a printer, a projector, or the like, or a combination thereof. Examples of the display device may include a liquid crystal display (LCD), a light-emitting diode (LED)-based display, a flat panel display, a curved screen, a television device, a cathode ray tube (CRT), a touch screen, or the like, or a combination thereof.

The communication port 740 may be connected to a network (e.g., the network 120) to facilitate data communications. The communication port 740 may establish connections between the processing engine 140 and the X-ray scanner 110, the terminal(s) 130, and/or the storage device 150. The connection may be a wired connection, a wireless connection, any other communication connection that can enable data transmission and/or reception, and/or any combination of these connections. The wired connection may include, for example, an electrical cable, an optical cable, a telephone wire, or the like, or any combination thereof. The wireless connection may include, for example, a Bluetooth™ link, a Wi-Fi™ link, a WiMax™ link, a WLAN link, a ZigBee link, a mobile network link (e.g., 3G, 4G, 5G, etc.), or the like, or a combination thereof. In some embodiments, the communication port 740 may be and/or include a standardized communication port, such as RS232, RS485, etc. In some embodiments, the communication port 740 may be a specially designed communication port. For example, the communication port 740 may be designed in accordance with the digital imaging and communications in medicine (DICOM) protocol.

Figure 8:
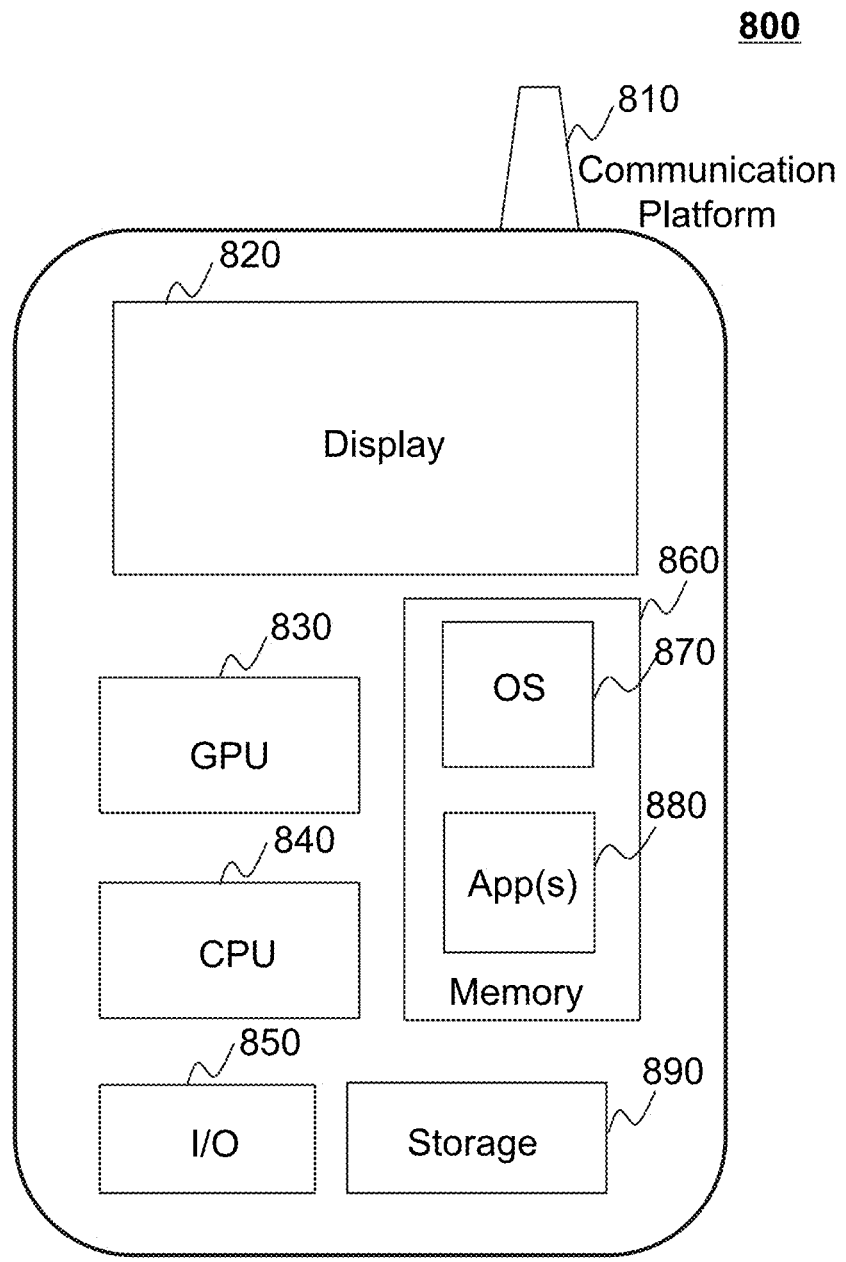
FIG. 8 is a schematic diagram illustrating exemplary hardware and/or software components of an exemplary mobile device on which one or more terminals may be implemented according to some embodiments of the present disclosure.

FIG. 8 is a schematic diagram illustrating exemplary hardware and/or software components of an exemplary mobile device 800 on which the terminal(s) 130 may be implemented according to some embodiments of the present disclosure. As illustrated in FIG. 8, the mobile device 800 may include a communication platform 810, a display 820, a graphic processing unit (GPU) 830, a central processing unit (CPU) 840, an I/O 850, a memory 860, and a storage 890. In some embodiments, any other suitable component, including but not limited to a system bus or a controller (not shown), may also be included in the mobile device 800. In some embodiments, a mobile operating system 870 (e.g., iOS™, Android™, Windows Phone™, etc.) and one or more applications 380 may be loaded into the memory 860 from the storage 890 in order to be executed by the CPU 840. The applications 880 may include a browser or any other suitable mobile apps for receiving and rendering information relating to image processing or other information from the processing engine 140. User interactions with the information stream may be achieved via the I/O 850 and provided to the processing engine 140 and/or other components of the X-ray scanner positioning system 100 via the network 120.

To implement various modules, units, and their functionalities described in the present disclosure, computer hardware platforms may be used as the hardware platform(s) for one or more of the elements described herein. A computer with user interface elements may be used to implement a personal computer (PC) or any other type of work station or terminal device. A computer may also act as a server if appropriately programmed.

Figure 9:
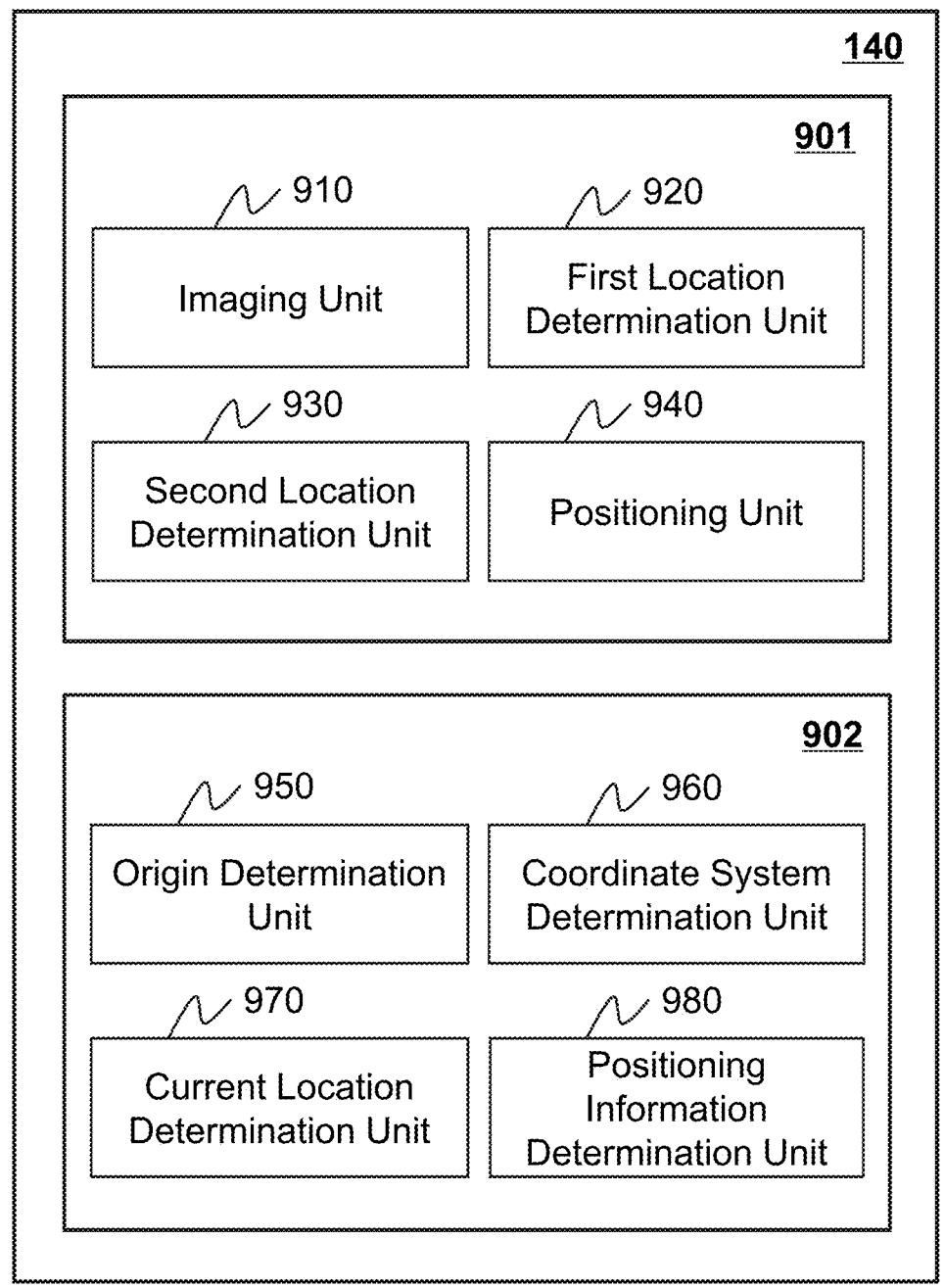
FIG. 9 is a schematic block diagram illustrating an exemplary processing engine according to some embodiments of the present disclosure.

FIG. 9 is a schematic block diagram illustrating an exemplary processing engine 140 according to some embodiments of the present disclosure. The processing engine 140 may include a first positioning module 901 and/or a second positioning module 902. Alternatively, the first positioning module 901 and the second positioning module 902 may be implemented in two processing engines, respectively.

The first positioning module 901 may be configured to determine positioning information of the indicator or the X-ray source 30 of the X-ray scanner 110. The positioning information of the indicator may guide the indicator to be positioned at a location to indicate a target position (e.g., as described in connection with FIGS. 11-15). The positioning information of the X-ray source 30 may guide the X-ray source 30 to be positioned at a location to allow a target in the object to remain in an imaging view, or a desired portion thereof, of the X-ray scanner 110 (e.g., as described in connection with FIGS. 16-22). For instance, the positioning information of the X-ray source 30 of the X-ray scanner 110 may guide the X-ray source 30 to be positioned at a location such that the target in the object remains in a center portion of the imaging view of the X-ray scanner 110. The first positioning module 901 may include an imaging unit 910, a first location determination unit 920, a second location determination unit 930, and a positioning unit 940.

The imaging unit 910 may be configured to obtain one or more images of an object scanned by the X-ray scanner 110. In some embodiments, the image of the object may be a 2D image or a 3D image. In some embodiments, the imaging unit 910 may obtain imaging data generated by the X-ray scanner 110 and generate one or more images of the object based on the imaging data. In some embodiments, the imaging unit 910 may generate one or more images of the object in advance and store the one or more images in the storage device 150 and/or a storage apparatus (e.g., the storage 720, the storage 890, or the memory 860). The imaging unit 910 may retrieve the one or more images from the storage device 150 and/or the storage apparatus (e.g., the storage 720, the storage 890, or the memory 860).

The first location determination unit 920 may be configured to determine an image target location of a target corresponding to the object. As used herein, a target may refer to a portion of an object (e.g., C illustrated in FIGS. 13 and 15), depending on the context where it is used.

The X-ray scanner 110 may scan a region of interest (ROI) of the object. The ROI of the object may be a portion of the object. For example, the object may be a patient. The ROI of the object may include a lung of the patient. The target may represent the ROI. The target may be a spot or an area in the ROI of the object. For example, the target may be a center point of the ROI. As another example, the target may be an area within the ROI. The image target location corresponding to the target may refer to a location of a portion of the image that corresponds to the target. In some embodiments, if the target is a spot in the object, the image target location may include the location of one or more neighboring pixels or voxels in an image corresponding to the target acquired by a scanning by the X-ray scanner 110. In some embodiments, if the target is an area in the object, the image target location may be the location of an area including a plurality of neighboring pixels or voxels in an image corresponding to the target acquired by a scanning by the X-ray scanner 110. As used herein, two pixels or voxels are considered neighboring pixels or voxels when they are next to each other without a pixel or voxel located in between. As used herein, more than two pixels or voxels in an area are considered neighboring pixels or voxels when each pixel or voxel in the area has at least one neighboring pixel or voxel within the area.

When one or more projection lines (e.g., the X-rays emitted from the X-ray source 30) emitted from a point (e.g., the X-ray source 30) pass through the target, the target may be projected onto a projection plane (e.g., the detector 20) and a pattern of the target may be generated on the projection plane (e.g., the detector 20). The pattern of the target generated on the projection plane (e.g., the detector 20) may be referred to as the center projection of the target.

In some embodiments, the X-ray source 30 may emit X-rays. One or more X-rays may pass through the target. The detector 20 may detect light signals relating to the X-rays passing through the target. An image including the target may be generated based on the light signals. As used herein, an image target location may be same as a center projection of the target onto the detector 20, depending on the context where the term is used. In some embodiments, the image target location may be identified by two-dimensional (2D) coordinates or three-dimensional (3D) coordinates.

The second location determination unit 930 may be configured to determine a target position of the target. The target position of the target may refer to an actual location of the target in space. The target position of the target may be identified by 2D coordinates or 3D coordinates.

The positioning unit 940 may be configured to determine positioning information of the indicator or the X-ray source 30 of the X-ray scanner 110 based on the target position of the target. In some embodiments, the positioning unit 940 may determine the positioning information of the indicator of the X-ray scanner 110. The positioning information of the indicator of the X-ray scanner 110 may guide the indicator to be positioned at a location to indicate the target position (e.g., as described in connection with FIGS. 11-15). In some embodiments, the positioning unit 940 may determine the positioning information of the X-ray source 30 of the X-ray scanner 110. The positioning information of the X-ray source 30 of the X-ray scanner 110 may guide the X-ray source 30 to be positioned at a location to allow the target in the object to remain in an imaging view of the X-ray scanner 110 (e.g., as described in connection with FIGS. 16-22).

The second positioning module 902 may be configured to determine positioning information of the X-ray scanner 110. The positioning information of the X-ray scanner 110 may guide the X-ray scanner 110 to move from one location to another location (e.g., as described in connection with FIG. 23). The second positioning module 902 may include an origin determination unit 950, a coordinate system determination unit 960, a current location determination unit 970, and a positioning information determination unit 980.

The origin determination unit 950 may be configured to determine an origin to determine a coordinate system. The coordinate system determination unit 960 may determine a coordinate system based on the origin. The current location determination unit 970 may determine coordinates of the current location based on the origin and the coordinate system. The positioning information determination unit 980 may determine the positioning information of the X-ray scanner 110 based on the origin and the coordinates of the current location. The positioning information of the X-ray scanner 110 may guide the X-ray scanner 110 to move from the current location to the origin (e.g., as described in connection with FIG. 23).

In some embodiments, the X-ray scanner 110 and/or one or more components of the X-ray scanner 110 (e.g., the actuator, the indicator, or the X-ray source 30) may be driven manually or automatically based on the positioning information of the X-ray scanner 110. For example, the processing engine 140 may transmit instructions relating to automatically drive the X-ray scanner 110 and/or the one or more components of the X-ray scanner 110 (e.g., the actuator, the indicator, or the X-ray source 30) to the X-ray scanner 110 (e.g., a driving module in the X-ray scanner 110) based on the positioning information.

The modules and/or units in the processing engine 140 may be connected to or communicate with each other via a wired connection or a wireless connection. The wired connection may include a metal cable, an optical cable, a hybrid cable, or the like, or any combination thereof. The wireless connection may include a Local Area Network (LAN), a Wide Area Network (WAN), a Bluetooth, a ZigBee, a Near Field Communication (NFC), or the like, or any combination thereof. Two or more of the units may be combined into a single unit, and any one of the units may be divided into two or more units. For example, the first location determination unit 920 may be integrated into the second location determination unit 930 as a single unit which may both determine the image target location and the target position. As another example, the imaging unit 910 may be divided into two units. The first unit may be configured to obtain the imaging data and/or the one or more images, while the second unit may be configured to generate one or more images based on the imaging data.

Figure 10:
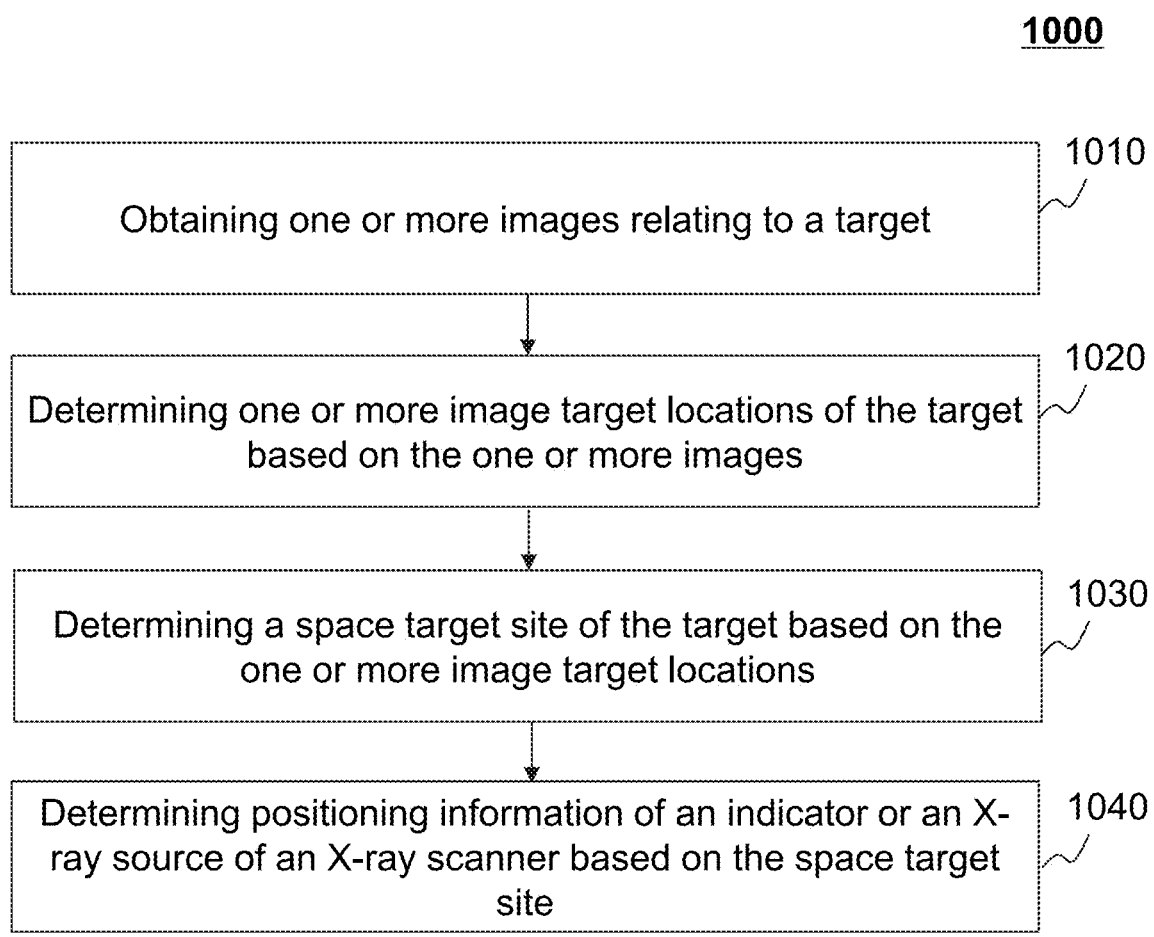
FIG. 10 is a flowchart illustrating an exemplary process for determining positioning information of an indicator or an X-ray source of an X-ray scanner according to some embodiments of the present disclosure.

FIG. 10 is a flowchart illustrating an exemplary process/method 1000 for determining positioning information of an indicator or an X-ray source of the X-ray scanner 110 according to some embodiments of the present disclosure. In some embodiments, the process/method 1000 may be implemented in the system 100 illustrated in FIG. 1. For example, the process/method 1000 may be stored in the storage device 150 and/or the storage apparatus (e.g., the storage 720, the storage 890, or the memory 860) in the form of instructions, and invoked and/or executed by the processing engine 140 (e.g., the processor 710 of the processing engine 140, one or more modules in the processing engine 140 illustrated in FIG. 9, or one or more units in the processing engine 140 illustrated in FIG. 9). The operations of the illustrated process/method presented herein are intended to be illustrative. In some embodiments, the process/method 1000 may be accomplished with one or more additional operations not described, and/or without one or more of the operations discussed. Additionally, the order in which the operations of the process/method 1000 as illustrated in FIG. 10 and described below is not intended to be limiting.

In 1010, the imaging unit 910 may obtain one or more images relating to a target. The target may refer to a portion of an object.

In 1020, the first location determination unit 920 may determine one or more image target locations of the target based on the one or more images. The image target location of the target may refer to a location of a portion of an image (e.g., one or more pixels or voxels in the image) corresponding to the target. For example, C' illustrated in FIG. 13 may be the image target location of the target C. As another example, $C_1$ illustrated in FIG. 20A may be the image target location of the target R.

In 1030, the second location determination unit 930 may determine the target position of the target based on the one or more image target locations. The target position may refer to an actual location of the target in space. The target position may be identified using 2D or 3D coordinates of a 2D or 3D coordinate system.

In 1040, the positioning unit 940 may determine positioning information on the basis of which the X-ray scanner 110 may be positioned at a location associated with the target position. In some embodiments, the positioning unit 940 may determine the positioning information of the indicator of the X-ray scanner 110. The positioning information of the indicator of the X-ray scanner 110 may guide the indicator to be positioned at a location to indicate the target position (e.g., as described in connection with FIGS. 11-15). In some embodiments, the positioning unit 940 may determine the positioning information of the X-ray source 30 of the X-ray scanner 110. The positioning information of the X-ray source 30 of the X-ray scanner 110 may guide the X-ray source 30 to be positioned at a location to allow the target in the object to remain in an imaging view, or a desired portion thereof, of the X-ray scanner 110 (e.g., as described in connection with FIGS. 16-22). For instance, the positioning information of the X-ray source 30 of the X-ray scanner 110 may guide the X-ray source 30 to be positioned at a location to allow the target in the object to remain in a center portion of the imaging view of the X-ray scanner 110.

Figure 11:
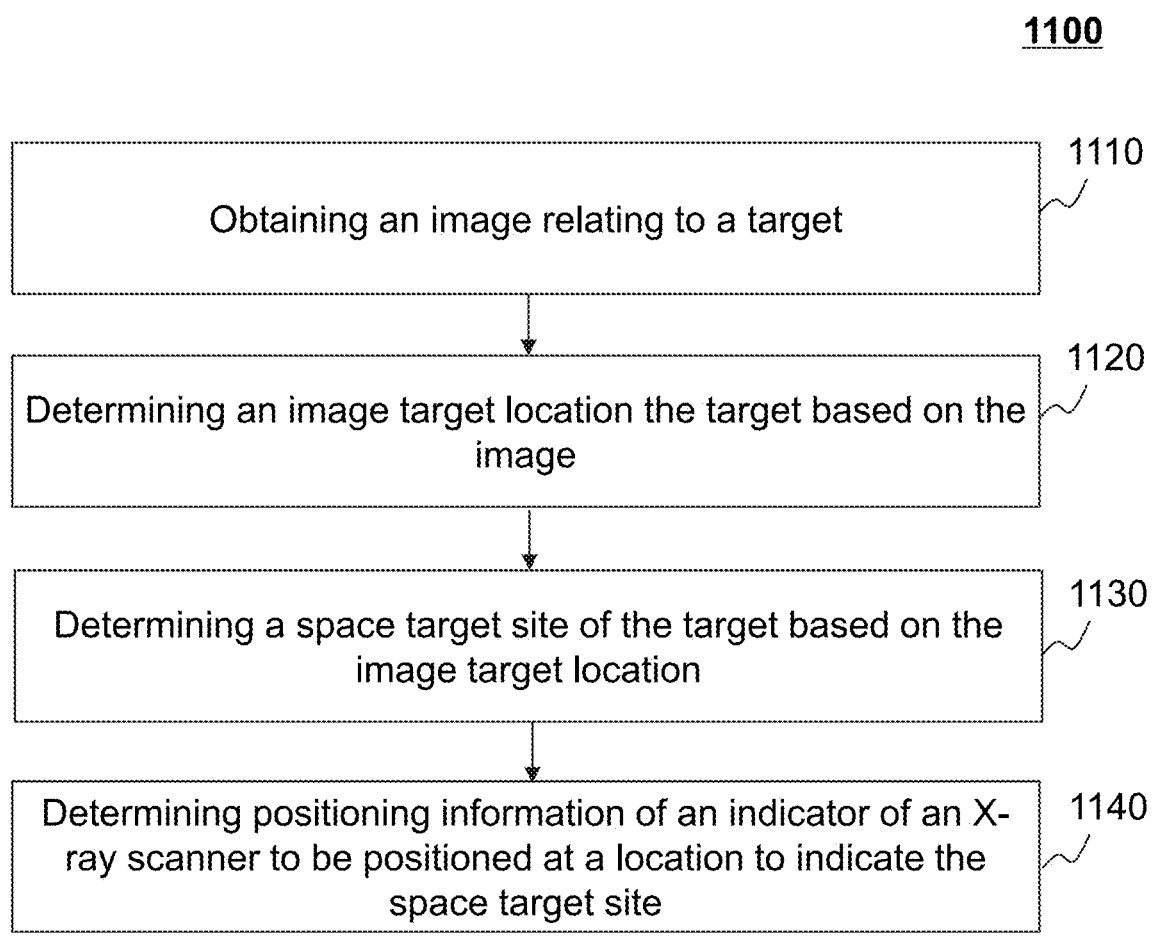
FIG. 11 is a flowchart illustrating an exemplary process for determining positioning information of an indicator of an X-ray scanner according to some embodiments of the present disclosure.

FIG. 11 is a flowchart illustrating an exemplary process/method 1100 for determining positioning information of an indicator of the X-ray scanner 110 according to some embodiments of the present disclosure. In some embodiments, the process/method 1100 may be implemented in the system 100 illustrated in FIG. 1. For example, the process/method 1100 may be stored in the storage device 150 and/or a storage apparatus (e.g., the storage 720, the storage 890, or the memory 860) in the form of instructions, and invoked and/or executed by the processing engine 140 (e.g., the processor 710 of the processing engine 140, one or more modules in the processing engine 140 illustrated in FIG. 9, or one or more modules in the processing engine 140 illustrated in FIG. 9). The operations of the illustrated process/method presented below are intended to be illustrative. In some embodiments, the process/method 1100 may be accomplished with one or more additional operations not described, and/or without one or more of the operations discussed. Additionally, the order in which the operations of the process/method 1100 as illustrated in FIG. 11 and described below is not intended to be limiting.

In some embodiments, when the X-ray scanner 110 includes an indicator, the processing engine 140 may perform the process/method 1100 to determine positioning information of the indicator. The positioning information of the indicator may be used to guide the indicator to be positioned at a location to indicate a target position of a target.

In 1110, the imaging unit 910 may obtain an image associated with the object. In some embodiments, the imaging unit 910 may obtain imaging data generated by the X-ray scanner 110 and generate the image associated with the object based on the imaging data. In some embodiments, the imaging unit 910 may generate the image associated with the object in advance and store the image in the storage device 150 and/or the storage apparatus (e.g., the storage 720, the storage 890, or the memory 860). The imaging unit 910 may obtain the image associated with the object from the storage device 150 and/or the storage apparatus (e.g., the storage 720, the storage 890, or the memory 860).

In 1120, the first location determination unit 920 may determine an image target location corresponding to a target to be imaged. The target may be a point or an area that represents an ROI of the object. For example, if the object is a patient, the ROI of the object may include a lung of the patient. The target may be a center point of the lung. The image target location may refer to the location of the portion of the image that corresponds to the target. The image target location may be identified by 2D coordinates in a 2D coordinate system. In some embodiment, the 2D coordinate system may be determined based on the image (or the detector 20). For example, the origin of the 2D coordinate system may be a top point in the bottom-left corner of the image (or the detector 20), the X axis of the 2D coordinate system may be an edge of the image (or the detector 20) that goes through the origin, and the Y axis of the 2D coordinate system may be another edge of the image (or the detector 20) that goes through the origin.

In some embodiments, after obtaining the image, the processing engine 140 may display the image on a screen. A user of the system 100 (e.g., a doctor or an imaging specialist) may determine the image target location. The determination of the image target location may be provided to the system 100 via a user interface by, for example, clicking a mouse or touching a screen. The user interface may be implemented on a computing device as illustrated in FIG. 7 or a mobile device as illustrated in FIG. 8. Based on the instruction as to the image target location, the first location determination unit 920 may determine 2D coordinates of the image target location. In some embodiments, the first location determination unit 920 may determine the image target location automatically based on, for example, an image recognition algorithms.

Merely by way of example, the target is a spot in an object corresponding to one or more pixels or voxels in an image acquired by a scanning by the X-ray scanner 110, and the first location determination unit 920 may identify the image target location by 2D coordinates of the one or more pixels or voxels. As another example, the target is an area corresponding to a plurality of neighboring pixels or voxels in an image acquired by a scanning by the X-ray scanner 110, and the first location determination unit 920 may select at least two pixels or voxels in the image corresponding to the target, and identify the image target location by 2D coordinates of the at least two pixels or voxels.

In 1130, the second location determination unit 930 may determine a target position of the target based on the image target location. In some embodiments, the second location determination unit 930 may identify the target position of the target by an orthographic projection of the target onto the detector 20. The target position of the target may be represented by 2D coordinates in a 2D coordinate system corresponding to the 2D coordinate system relating to the image target location.

Merely by way of example, the target is a spot in an object corresponding to one or more neighboring pixels or voxels in an image acquired by a scanning by the X-ray scanner 110, and the second location determination unit 930 may determine the target position of the target based on the 2D coordinates of the one or more pixels or voxels. As another example, the target is an area corresponding to a plurality of neighboring pixels or voxels in an image acquired by a scanning by the X-ray scanner 110, and the second location determination unit 930 may determine the target position of the target based on the 2D coordinates of at least two pixels or voxels corresponding to two spots within the target.

Figure 12:
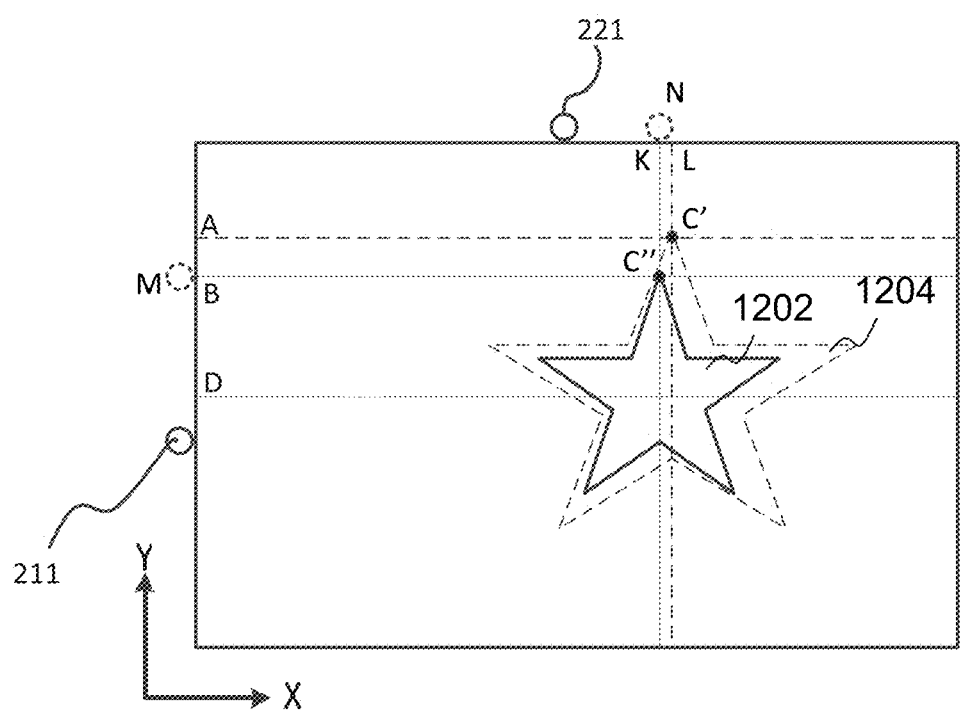
FIGS. 12 through 15 are schematic diagrams illustrating exemplary processes for determining a target position of a target according to some embodiments of the present disclosure.

In some embodiments, the second location determination unit 930 may determine the coordinates of the target position by determining coordinates of an orthographic projection of the target onto the detector 20 (e.g., C" illustrated in FIG. 12). When one or more projection lines that are parallel to each other and vertical to a projection plane (e.g., the detector 20) pass through the target, the target may be projected onto the projection plane (e.g., the detector 20) and a pattern of the target may be generated on the projection plane (e.g., the detector 20). The pattern of the target generated on the projection plane (e.g., the detector 20) may be referred to as the orthographic projection of the target.

In 1140, the positioning unit 940 may determine positioning information of the indicator of the X-ray scanner 110. The indicator may be positioned at a location according to the positioning information to indicate the target position. In some embodiments, positioning information of the indicator of the X-ray scanner 110 may guide the indicator to move from a current location of the indicator to a location such that the indicator may indicate the target position. In some embodiments, the indicator may be moved to the location manually, or automatically by the processing engine 140 or a driving module of the X-ray scanner 110 based on the positioning information of the indicator. The processing engine 140 may transmit instructions relating to automatically drive the indicator to the X-ray scanner 110 (e.g., the driving module of the X-ray scanner 110) based on positioning information. For brevity, some examples of the process/method 1100 may be provided. It should be noted that the examples are merely provided for the purposes of illustration, and not intended to limit the scope of the present disclosure.

Figure 13:
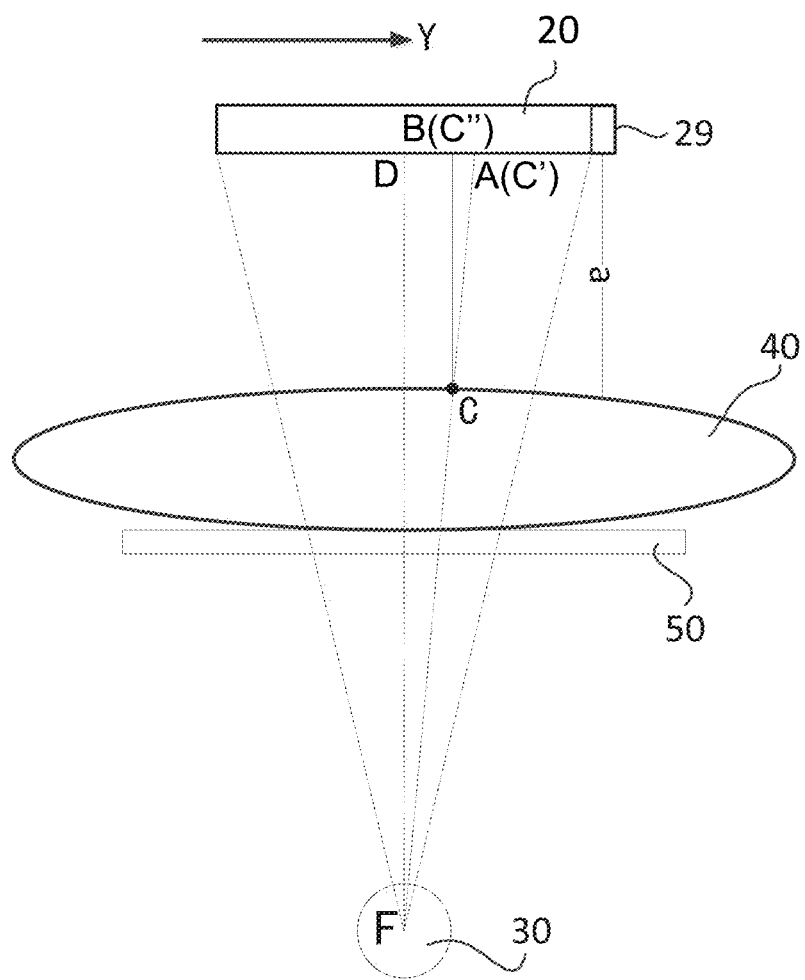

FIGS. 12 and 13 are schematic diagrams illustrating an exemplary process for determining a target position of a target according to some embodiments of the present disclosure. In some embodiments, the exemplary process may be applied to the indicator illustrated in FIGS. 3A and 3B and a target in an object that is a spot corresponding to one or more neighboring pixels or voxels in an image acquired by a scanning by the X-ray scanner 110.

As shown in FIGS. 12 and 13, 40 may refer to the object. A table 50 may support the object to be scanned. A dotted star 1204 may refer to a location in the image of the ROI (e.g., a center projection of the ROI onto the detector 20). A solid star 1202 may refer to a location in space of the ROI (e.g., an orthographic projection of the ROI onto the detector 20). C may refer to a target in the object 40 that is a spot corresponding to one or more pixels or voxels in an image of the object 40 acquired by a scanning by the X-ray scanner 110. The X-ray source 30 may emit X-rays. The X-rays may pass through the target C and be detected by the detector 20. C' may refer to the image target location of the target C (e.g., a center projection of the target C onto the detector 20). C" may refer to the target position of the target C (e.g., an orthographic projection of the target C onto the detector 20). A may refer to a Y coordinate of C'. L may refer to an X coordinate of C'. B may refer to a Y coordinate of C". K may refer to an X coordinate of C". D may refer to a Y coordinate of a midpoint of an image edge parallel to the Y axis illustrated in FIG. 12. The reference numeral 211 may refer to a first linear laser light. The reference numeral 221 may refer to a second linear laser light. The reference numeral 29 may refer to a rangefinder configured to determine a distance between two points. For example, the rangefinder 29 may determine a distance between the object 40 and the detector 20. F illustrated in FIG. 13 may indicate a focus of the X-ray source 30.

The first linear laser light 211 may be actuated to a location (e.g., location M) of the detector 20 corresponding to the Y coordinate of C", and the second linear laser light 221 may be actuated to a location (e.g., location N) of the detector 20 corresponding to the X coordinate of C", such that the first linear laser light 211 and the second linear laser light 221 may indicate the target position of the target C (e.g., C").

For illustration purposes and not intended to limit the scope of the present disclosure, a process for determining the Y coordinate of C" is provided with reference to FIG. 13. As shown in FIG. 13, to determine the length of AB, the Y coordinate of C" may be determined. As shown in FIG. 13, ΔABC and ΔADF may be similar (e.g., ΔABC∽ΔADF). The second location determination unit 930 may determine the Y coordinate of C" based on Equation (1) below:

$$\frac{L_{AB}}{L_{AD}} = \frac{L_{BC}}{L_{DF}}, \tag{1}$$

where $L_{AB}$ refers to the length of AB, $L_{AD}$ refers to the length of AD, $L_{BC}$ refers to the length of BC, and $L_{DF}$ refers to the length of DF.

The Y coordinate of C' is known, so $L_{AD}$ is known. The second location determination unit 930 may determine $L_{BC}$ by determining a distance between the object 40 and the detector 20 using the rangefinder 29. For example, the rangefinder 29 may determine that the distance between the object 40 and the detector 20 is equal to a, and the second location determination unit 930 may determine $L_{BC}$ as a as illustrated in FIG. 13. $L_{DF}$ may refer to a distance between the X-ray source 30 and the detector 20 and be known for the X-ray scanner 110. In some embodiments, the second location determination unit 930 may determine the Y coordinate of C" based on $L_{AB}$. In some embodiments, the second location determination unit 930 may determine the X coordinate of C" based on the same process as the process for determining the Y coordinate of C".

Figure 14:
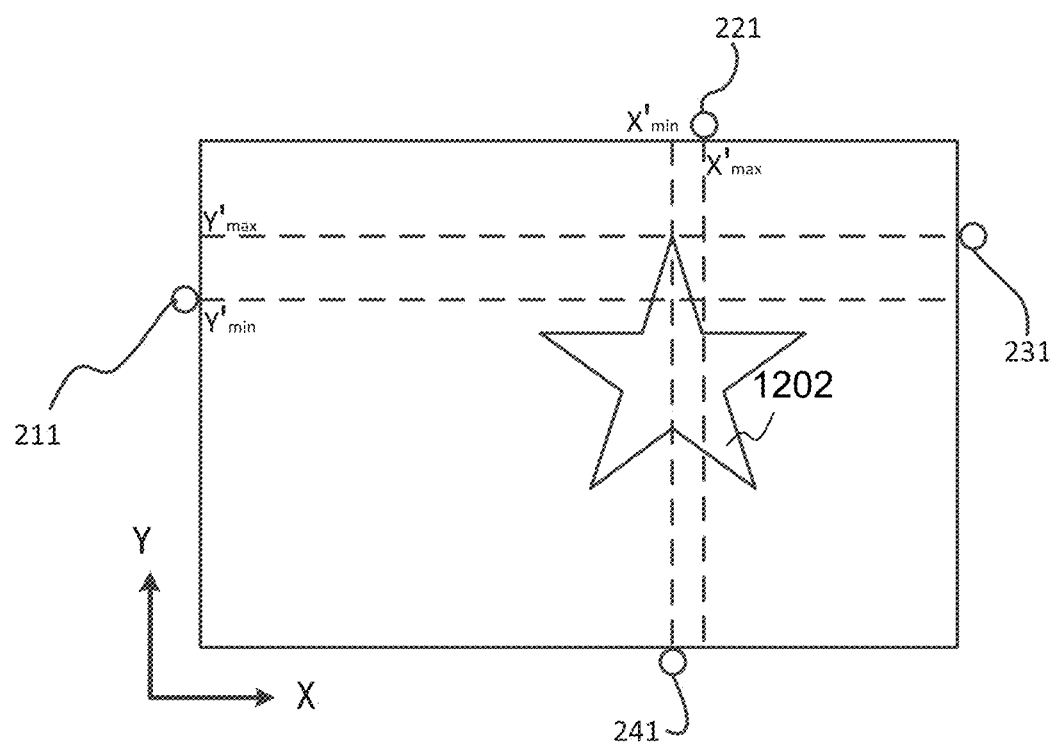

FIG. 14 is a schematic diagram illustrating an exemplary process for determining a target position of a target according to some embodiments of the present disclosure. In some embodiments, the exemplary process may be applicable to the indicator illustrated in FIG. 4 and a target in an object that is an area corresponding to a plurality of neighboring pixels or voxels in an image acquired by a scanning by the X-ray scanner 110.

As shown in FIG. 14, $X_{max}'$ may refer to a maximum X coordinate of the target position of the target that is an area. $X_{min}'$ may refer to a minimum X coordinate of the target position of the target. $Y_{max}'$ may refer to a maximum Y coordinate of the target position of the target. $Y_{min}'$ may refer to a minimum Y coordinate of the target position of the target.

The maximum X coordinate, the minimum X coordinate, the maximum Y coordinate, and the minimum Y coordinate of the target position may be determined. The first linear laser light 211 may be actuated to a location of the detector 20 corresponding to $Y_{min}'$, the third linear laser light 231 may be actuated to a location of the detector 20 corresponding to $Y_{max}'$, the second linear laser light 221 may be actuated to a location of the detector 20 corresponding to $X_{max}'$, and the fourth linear laser light 241 may be actuated to a location of the detector 20 corresponding to $X_{min}'$, such that laser rays emitted from the first linear laser light 211, the second linear laser light 221, the third linear laser light 231, and the fourth linear laser light 241 may define an area to indicate the target position of the target that is an area.

In some embodiments, the second location determination unit 930 may determine $X_{min}'$, $X_{max}'$, $Y_{min}'$, and $Y_{max}'$ based on the same process as the process of determining the Y coordinate of C" illustrated in FIGS. 13-14 and the description thereof.

Figure 15:
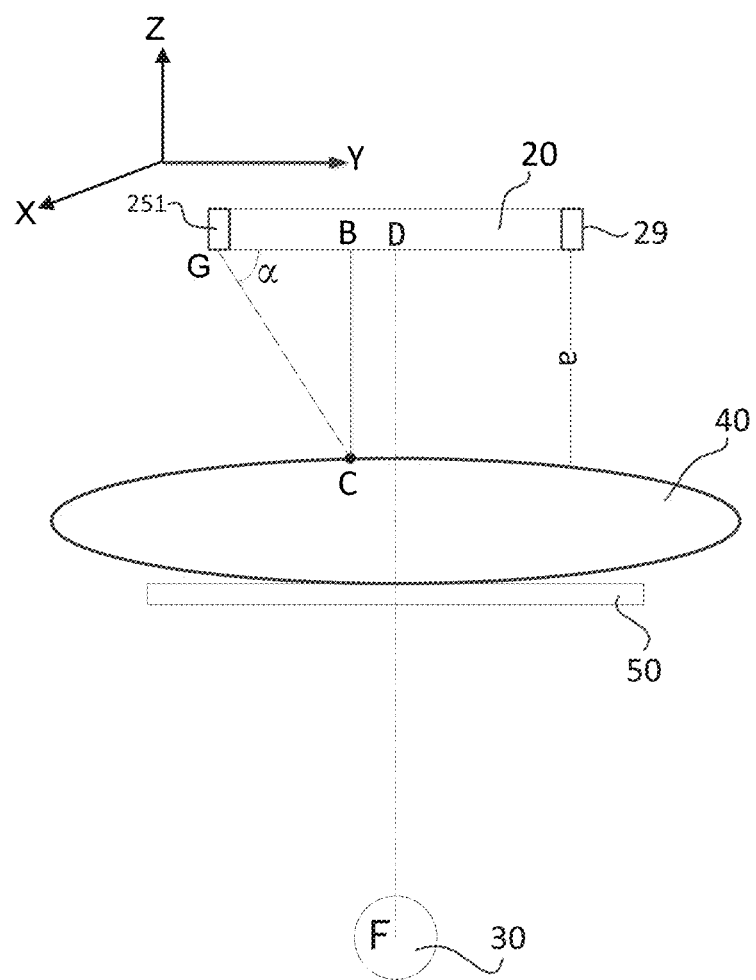

FIG. 15 is a schematic diagram illustrating an exemplary process for determining the target position of a target according to some embodiments of the present disclosure. In some embodiments, the exemplary process 1100 may be applicable to the indicator illustrated in FIGS. 5A and 6 and a target in an object that is a spot corresponding to one or more neighboring pixels or voxels in an image acquired by a scanning by the X-ray scanner 110.

As shown in FIG. 15, 251 may refer to a fifth laser light described in FIG. 5A and/or FIG. 6. The fifth actuator unit may actuate the fifth laser light 251 to swing. In some embodiments, a rotation may refer to a movement along a circle. A swing may refer to a movement along a part of a circle (e.g., an arc). α may refer to a swing angle of the fifth laser light 251.

The Y coordinate of the target position of the target C, and the swing angle of the fifth laser light 251 may be determined. The fifth laser light 251 may be actuated to a location of the detector 20 corresponding to the Y coordinate of the target position of the target C and to a swing angle equal to α, such that the fifth laser light 251 may indicate the target position of the target C.

In some embodiments, the second location determination unit 930 may determine the Y coordinate of the target position of the target C based on the same process as the process for determining the Y coordinate of C" in the image as illustrated in FIGS. 12 and 13 and the description thereof.

In some embodiments, the second location determination unit 930 may determine a based on Equation (2) below:

$$\tan \alpha = \frac{L_{BC}}{L_{BG}}, \quad (2)$$

wherein $L_{BC}$ refers to the length of BC, $L_{BG}$ refers to the length of BG, and G refer to a spot in the fifth laser light 251 and represents the fifth laser light 251.

The second location determination unit 930 may determine $L_{BZ}$ based on the Y coordinate of the target position of the target C. The second location determination unit 930 may determine $L_{BC}$ by determining a distance between the object 40 and the detector 20 using the rangefinder 29.

Alternatively, the second location determination unit 930 may determine an X coordinate of the target position of the target C and a swing angle of β to make the fifth laser light 251 indicate the target position of the target C.

Figure 16:
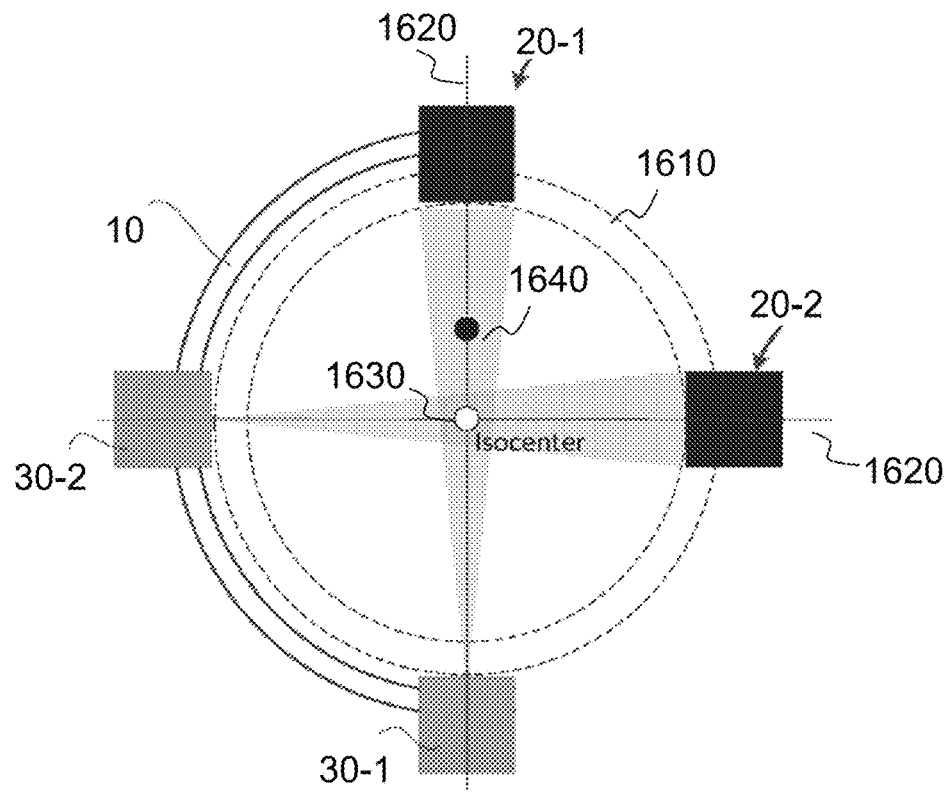
FIG. 16 is a schematic diagram illustrating an isocentric rotation of an X-ray scanner according to some embodiments of the present disclosure.

FIG. 16 is a schematic diagram illustrating an isocentric rotation of the X-ray scanner 110 according to some embodiments of the present disclosure. As shown in FIG. 16, when the support 10 undergoes an isocentric rotation, a center line 1620 of the X-rays emitted from the X-ray source 30 passes through the center 1630 of the support 10 of the X-ray scanner 110. For the isocentric rotation, the center of the support 10 may be referred to as an isocenter of the X-ray scanner 110. As shown in FIG. 16, during an isocentric rotation, unless a target 1640 is placed at the center 1630 of the support 10 of the X-ray scanner 110, the target 1640 may be out of an imaging view (e.g., a region in the pathway of the X-rays) of the X-ray scanner 110 when the support 10 undergoes an isocentric rotation from one location (e.g., 30-1) to another location (e.g., 30-2). A location 20-1 of the detector 20 may correspond to the location 30-1 of the X-ray source 30. A location 20-2 of the detector 20 may correspond to the location 30-2 of the X-ray source 30. The dotted line 1610 may refer to a rotation track of the detector 20 and/or the X-ray source 30.

Figure 17:
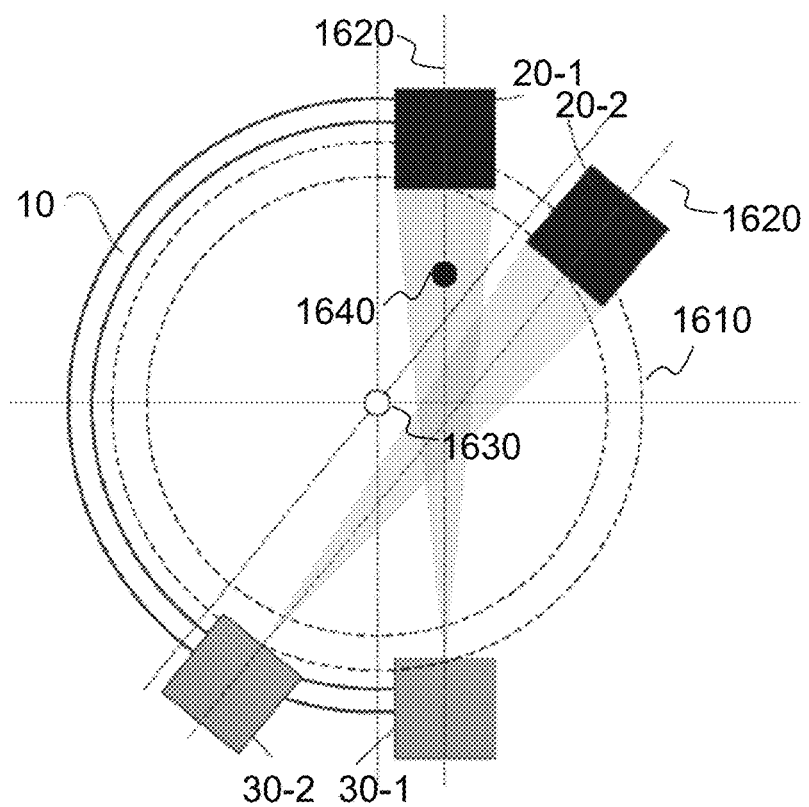
FIG. 17 is a schematic diagram illustrating a non-isocentric rotation of an X-ray scanner according to some embodiments of the present disclosure.

FIG. 17 is a schematic diagram illustrating a non-isocentric rotation of the X-ray scanner 110 according to some embodiments of the present disclosure. As shown in FIG. 17, when the support 10 undergoes a non-isocentric rotation, a center line 1620 of the X-rays emitted from the X-ray source 30 does not pass through the center 1630 of the support 10. As shown in FIG. 17, for the non-isocentric rotation, the target 1640 may be out of the imaging view (e.g., a region that is in the pathway of the X-rays) of the X-ray scanner 110 when the support 10 undergoes a non-isocentric rotation from one location to another location.

When the support 10 undergoes an isocentric rotation and/or a non-isocentric rotation from one location to another location, the processing engine 140 may determine positioning information of the X-ray source 30 to move the X-ray source 30 accordingly so as to allow a target of an object to remain in the imaging view, or a desired portion thereof, of the X-ray scanner 110. For instance, the positioning information of the X-ray source 30 of the X-ray scanner 110 may guide the X-ray source 30 to be positioned at a location such that the target in the object remains in a center portion of the imaging view of the X-ray scanner 110.

Figure 18:
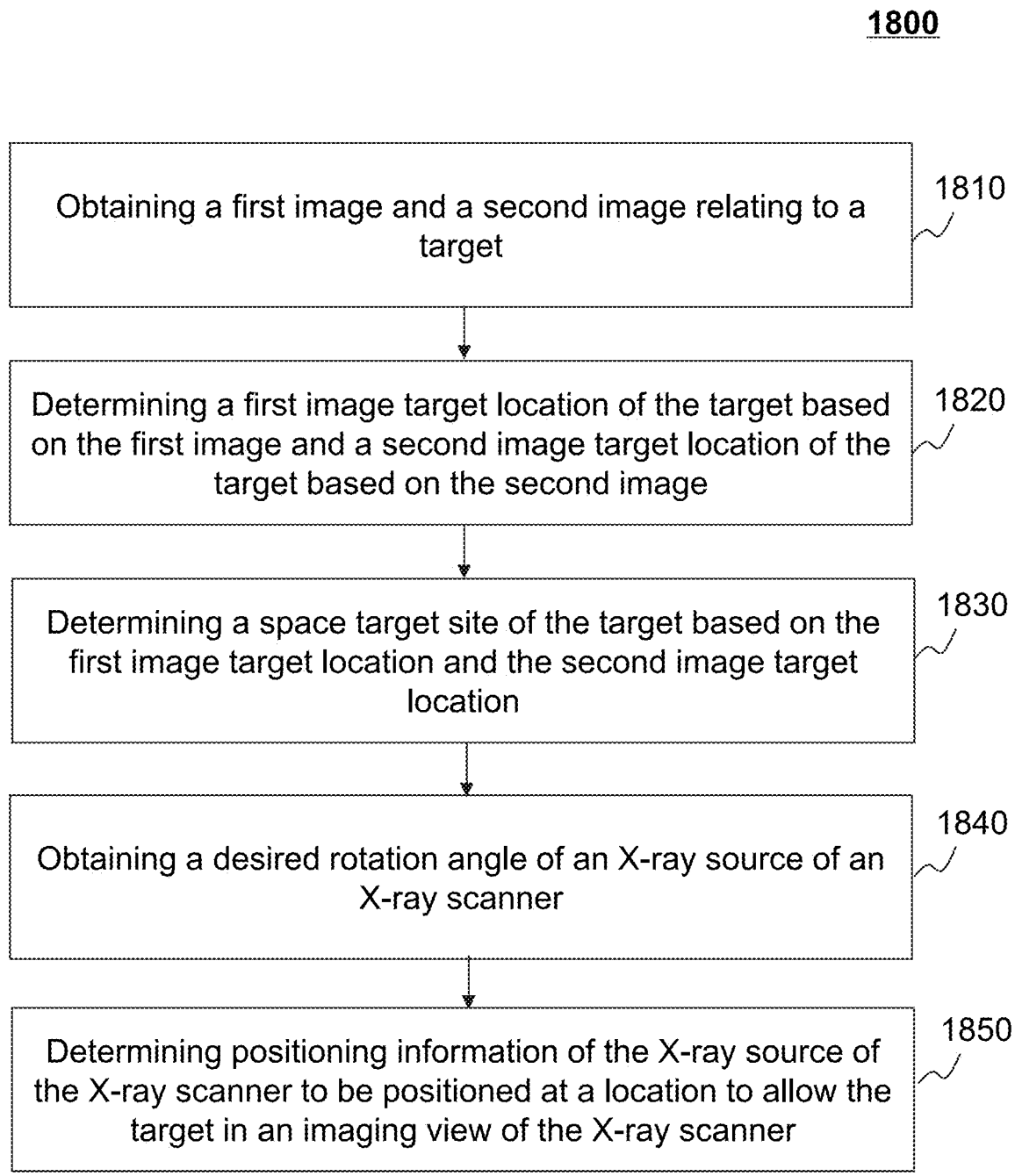
FIG. 18 is a flowchart illustrating an exemplary process for determining positioning information of an X-ray source of an X-ray scanner according to some embodiments of the present disclosure.

FIG. 18 is a flowchart illustrating an exemplary process/method 1800 for determining positioning information of the X-ray source 30 of the X-ray scanner 110 according to some embodiments of the present disclosure. In some embodiments, the process/method 1800 may be implemented in the system 100 illustrated in FIG. 1. For example, the process/method 1800 may be stored in the storage device 150 and/or a storage apparatus (e.g., the storage 720, the storage 890, or the memory 860) in the form of instructions, and invoked and/or executed by the processing engine 140 (e.g., the processor 710 of the processing engine 140, one or more modules in the processing engine 140 illustrated in FIG. 9, or one or more units in the processing engine 140 illustrated in FIG. 9). The operations of the illustrated process/method presented below are intended to be illustrative. In some embodiments, the process/method 1800 may be accomplished with one or more additional operations not described, and/or without one or more of the operations discussed. Additionally, the order in which the operations of the process/method 1800 as illustrated in FIG. 18 and described below is not intended to be limiting.

In some embodiments, the processing engine 140 may perform the process/method 1800 to determine positioning information of the X-ray source 30 of the X-ray scanner 110. The positioning information of the X-ray source 30 may guide the X-ray source 30 to be positioned at a location such that a target in an object is within the imaging view, or a desired portion thereof, of the X-ray scanner 110. The target may be part of an object scanned by the X-ray scanner 110. The target may be a spot or an area representing the ROI of the object.

In 1810, the imaging unit 910 may obtain a first image and a second image of an object. The X-ray source 30 may emit X-rays toward the object. The detector 20 may detect the X-rays emitted from the X-ray source 30 and generate imaging data used to generate one or more images associated with the object. In some embodiments, the imaging unit 910 may obtain imaging data generated by the X-ray scanner 110 and generate the first image and the second image of the object based on the imaging data. In some embodiments, the imaging unit 910 may generate the first image and the second image of the object in advance and store the first image and the second image in the storage device 150 and/or the storage apparatus (e.g., the storage 720, the storage 890, or the memory 860). The imaging unit 910 may obtain the first image and the second image from the storage device 150 and/or the storage apparatus (e.g., the storage 720, the storage 890, or the memory 860).

In some embodiments, the first image may be generated based on the imaging data generated when the X-ray source 30 scans the object at a first scanning location. The second image may be generated based on the imaging data generated when the X-ray source 30 scans the object at a second scanning location. In some embodiments, a scanning location of the X-ray source 30 may be identified using a rotation angle and a spatial location. The rotation angle may refer to an angle between a center line of the X-rays emitted from the X-rays source 30 and a straight line vertical to a horizontal plane. In some embodiments, the object subject to a scanning using the X-ray source 30 may be placed on the horizontal surface of a table (e.g., the table 50 as illustrated in FIG. 13 or FIG. 15). The spacial location of the X-ray source 30 may be identified using 3D coordinates. In some embodiments, the rotation angle of the first scanning location and the rotation angle of the second scanning location may be the same or different. Two scanning locations are considered the same if both the rotation angles and the spatial locations of the two scanning locations are the same. Two scanning locations are considered different if either the rotation angles or the spatial locations of the two scanning locations are different.

In some embodiments, the first location and/or the second location may be set manually by the user or automatically by the system 100 according to, for example, a default setting of the X-ray scanner 110.

In 1820, the first location determination unit 920 may determine a first image target location corresponding to the target based on the first image and a second image target location of the target based on the second image. The first location determination unit 920 may determine the first image target location of the target by identifying, in the first image, one or more pixels or voxels corresponding to the target. The first location determination unit 920 may determine the second image target location of the target by identifying, in the second image, one or more pixels or voxels corresponding to the target. In some embodiments, the first image target location and the second image target location may be identified by respective 3D coordinates in a 3D coordinate system.

In some embodiments, after obtaining the first image and the second image, the processing engine 140 may display the two images on a screen. A user of the system 100 (e.g., a doctor or an imaging specialist) may determine the first image target location and the second image target location by, for example, clicking a mouse or touching the screen. After receiving the instructions of determining the first image target location and the second image target location, the first location determination unit 920 may determine the 3D coordinates of the first image target location and the 3D coordinates of the second image target location. In some embodiments, after the first image target location is identified manually by the user, the first location determination unit 920 may determine the second image target location automatically based on the first image target location (e.g., the grey value of the first image target location). In some embodiments, the first location determination unit 920 may determine the first image target location and the second image target location automatically based on, for example, an image recognition algorithm to recognize the portion of the image (e.g., one or more pixels or voxels) corresponding to the target.

In some embodiments, the target is a spot in an object corresponding to one or more pixels or voxels in the first (or second) image acquired by a scanning by the X-ray scanner 110, the first (or second) image target location may be identified by 3D coordinates of the one or more pixels or voxels in the first (or second) image corresponding to the target. In some embodiments, the target is an area corresponding to a plurality of pixels or voxels in the first (or second) image acquired by a scanning by the X-ray scanner 110, the first location determination unit 920 may select at least two pixels or voxels in the first (or second) image, and the first (or second) image target location may be identified by 3D coordinates of the at least two pixels or voxels in the first (or second) image.

In 1830, the second location determination unit 930 may determine a target position of the target based on the first image target location and the second image target location. The target position of the target may be identified by 3D coordinates in a 3D coordinate system corresponding to the 3D coordinate system relating to the first image target location and/or the second image target location. In some embodiments, if the target is a spot, the target position of the target may be identified by the 3D coordinates of the target. In some embodiments, if the target is an area, the target position of the target may be identified by the 3D coordinates of at least two spot in the target. The at least two spot in the target may correspond to the at least two pixels or voxels in the first image and/or the second image of the target.

In 1840, the positioning unit 940 may determine a desired rotation angle of the X-ray source 30 of the X-ray scanner 110. The desired rotation angle of the X-ray source 30 may refer to a rotation angle of the X-ray source 30 to facilitate the scanning of an object. In some embodiments, the desired rotation angle may be set manually by the user. In some embodiments, the desired rotation angle may be determined automatically by the system 100 according to, for example, a default setting of the X-ray scanner 110.

In 1850, the positioning unit 940 may determine positioning information of the X-ray source 30. The positioning information of the X-ray source 30 may guide the X-ray source 30 to be positioned at a location so as to allow the target of the object to remain in the imaging view of the X-ray scanner 110. The positioning information of the X-ray source 30 may guide the X-ray source 30 to move from a current location of the X-ray source 30 to the location such that the target may be in the imaging view of the X-ray scanner 110. In some embodiments, the X-ray source 30 may be moved to the location manually, or automatically by, e.g., the processing engine 140 or a driving module of the X-ray scanner 110, based on the positioning information of the X-ray source 30.

In some embodiments, in addition to the target position of the target, the positioning unit 940 may determine the positioning information of the X-ray source 30 based on the desired location where the user desires the target to locate in the imaging view of the X-ray scanner 110. For example, the desired location of the target may be on or intercept the center line of the X-rays emitted from the X-ray source 30, and a distance between the target and the center of the detector 20 may be one-third of the length of the center line of the X-rays. The length of the center line of the X-rays may refer to a length of a segment from the focus of the X-ray source 30 to the center of the detector 20. The desired location of the target may be set manually by the user or automatically by the system 100 according to, for example, a default setting of the X-ray scanner 110.

FIG. 19 is a flowchart illustrating an exemplary process/method 1900 for determining the target position of a target according to some embodiments of the present disclosure. In some embodiments, the process/method 1900 may be implemented in the system 100 illustrated in FIG. 1. For example, the process/method 1900 may be stored in the storage device 150 and/or a storage apparatus (e.g., the storage 720, the storage 890, or the memory 860) in the form of instructions, and invoked and/or executed by the processing engine 140 (e.g., the processor 710 of the processing engine 140, or one or more modules in the processing engine 140 illustrated in FIG. 9). The operations of the illustrated process/method presented below are intended to be illustrative. In some embodiments, the process/method 1900 may be accomplished with one or more additional operations not described, and/or without one or more of the operations discussed. Additionally, the order in which the operations of the process/method 1900 as illustrated in FIG. 19 and described below is not intended to be limiting. In some embodiments, 1830 illustrated in FIG. 18 may be performed according to the process/method 1900.

The second location determination unit 930 may determine a first segment between the first image target location and the first scanning location of the X-ray source 30. In some embodiments, the second location determination unit 930 may determine a 3D straight-line equation of the first segment based on the 3D coordinates of the first scanning location and the 3D coordinates of the first target location.

The second location determination unit 930 may determine a second segment between the second image target location and the second scanning location of the X-ray source 30. In some embodiments, the second location determination unit 930 may determine a 3D straight-line equation of the second segment based on the 3D coordinates of the second scanning location and the 3D coordinates of the second target location.

The second location determination unit 930 may determine the target position based on the first segment and the second segment. In some embodiments, the second location determination unit 930 may determine the target position by determining an intersection of the first segment and the second segment. In some embodiments, for a condition that there is no intersection of the first segment and the second segment, the second location determination unit 930 may determine a third segment between a point of the first segment and a point of the second segment. There may be a plurality of segments between any one point of the first segment and any one point of the second segment. The second location determination unit 930 may designate the segment with the minimum length among the plurality of segments between the first segment and the second segment as the third segment. A segment of the plurality of segments includes a point in the first segment and a point in the second segment. The second location determination unit 930 may determine whether the length of the third segment is greater than a threshold. The second location determination unit 930 may designate a point of the third segment (e.g., a midpoint of the third segment) as the target position of the target in response to a determination that the length of the third segment is less than or equal to the threshold. The first location determination unit 920 may determine a new first image target location of the target and a new second image target location of the target in response to a determination that the length of the third segment is greater than the threshold. For example, the user may determine a new first image target location of the target and a new second image target location of the target by, for example, clicking a mouse or touching a screen in a user interface of the X-ray scanner positioning system 100.

For illustration purposes and not intended to limit the scope of the present disclosure, some examples for determining the target position of the target described in FIG. 18 and/or FIG. 19 are provided with reference to FIGS. 20A, 20B, 21, 22A, and 22B.

Figure 20A:
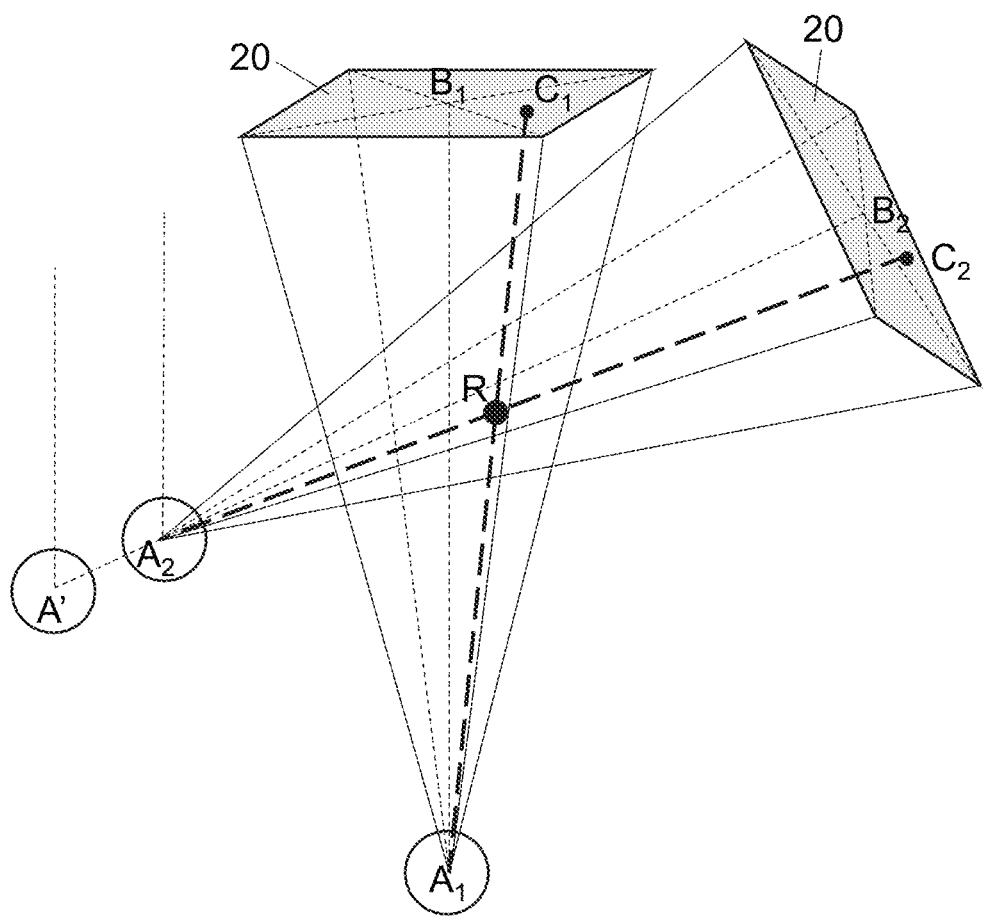
FIG. 20A is a schematic diagram illustrating an example for determining a target position of a target according to some embodiments of the present disclosure.

FIG. 20A is a schematic diagram illustrating a first example of the process/method 1800 and/or the process/method 1900 for determining a target position of a target according to some embodiments of the present disclosure. In some embodiments, the first example of determining the target position may be applicable to the target that is a spot corresponding to one or more neighboring pixels in an image of the object acquired by a scanning by the X-ray scanner 110. For example, the target may be a center of the ROI of the object. The rotation angle of the first scanning location and the rotation angle of the second scanning location may be different for a condition that the target is a spot.

As shown in FIG. 20A, $A_1$ may refer to a first scanning location of the X-ray source 30. $A_2$ may refer to a second scanning location of the X-ray source 30. R may refer to the target. $C_1$ may refer to the first image target location. $C_2$ may refer to the second image target location. $B_1$ may refer to the center of the first image (or the detector 20). $B_2$ may refer to the center of the second image (or the detector 20).

The second location determination unit 930 may determine a straight-line equation of $A_1C_1$ based on the 3D coordinates of $A_1$ and the 3D coordinates of $C_1$. The second location determination unit 930 may determine a straight-line equation of $A_2C_2$ based on the 3D coordinates of $A_2$ and the 3D coordinates of $C_2$. The second location determination unit 930 may determine the 3D coordinates of the target position of the target (e.g., R) by determining the 3D coordinates of an intersection of $C_1$ and $A_2C_2$.

Figure 20B:
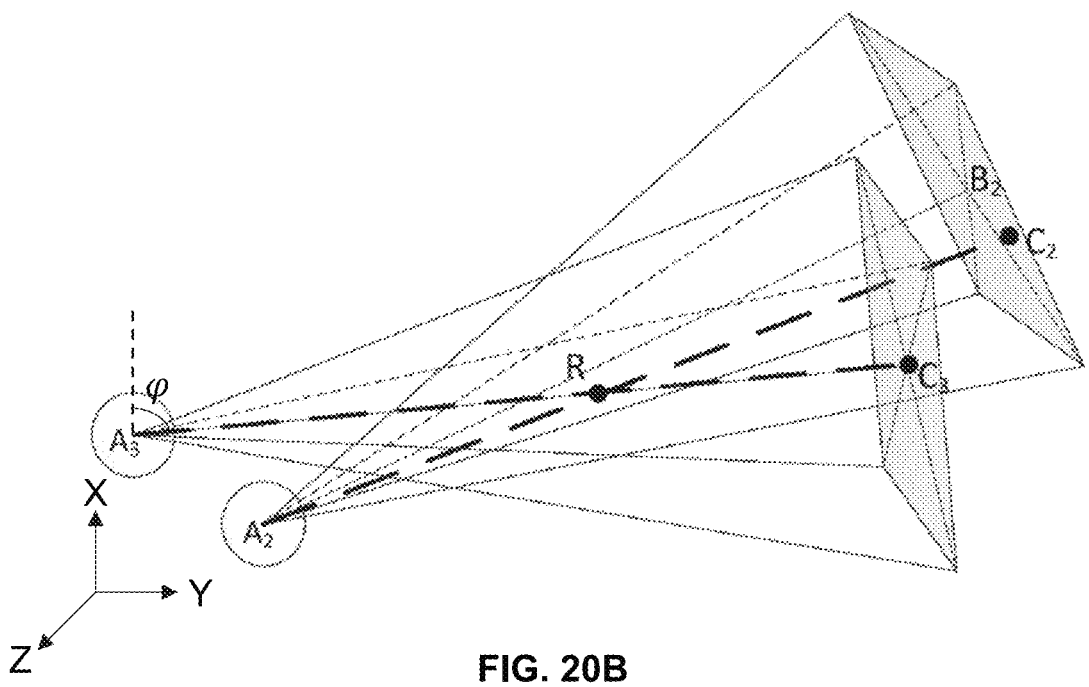
FIG. 20B is a schematic diagram illustrating an example for determining positioning information of an X-ray source according to some embodiments of the present disclosure.

FIG. 20B is a schematic diagram illustrating an example of determining positioning information of the X-ray source 30 according to some embodiments of the present disclosure.

As shown in FIG. 20B, φ may refer to a desired rotation angle of the X-ray source 30. After the second location determination unit 930 determines the target position of a target (e.g., R), the positioning unit 940 may determine the position information to move the X-ray source 30 such that the target remains in the imaging view (e.g., on or intercepting the center line $A_3C_3$ of the X-rays emitted from the X-ray source 30) of the X-ray scanner 110. For example, the positioning information of the X-ray source 30 may guide the X-ray source 30 to translate a distance along the X-axis direction shown in FIG. 20B from the current location (e.g., $A_2$). Additionally or alternatively, the positioning information of the X-ray source 30 may guide the X-ray source 30 to translate a distance along the Y-axis direction shown in FIG. 20B from the current location. Additionally or alternatively, the positioning information of the X-ray source 30 may guide the X-ray source 30 to translate a distance along the Z-axis direction shown in FIG. 20B from the current location.

Figure 21:
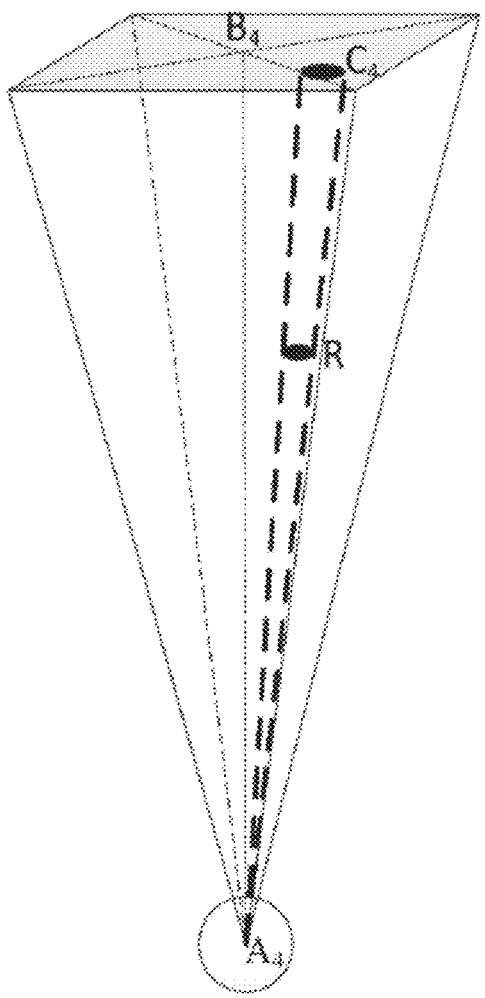
FIGS. 21, 22A, and 22B are schematic diagrams illustrating examples for determining a target position of a target according to some embodiments of the present disclosure.
Figure 22A:
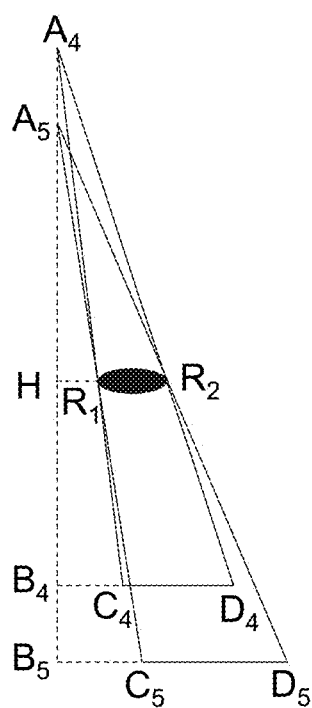
Figure 22B:
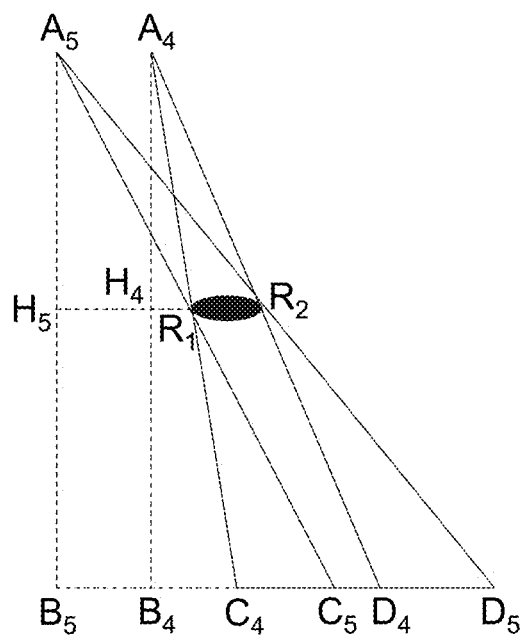

FIGS. 21, 22A, and 22B are schematic diagrams illustrating a second example of the process/method 1800 and/or the process/method 1900 for determining a target position corresponding to a target according to some embodiments of the present disclosure. In some embodiments, the second example for determining the target position may be applicable to the target that is an area. For example, as shown in FIG. 21, the target may be an area included in the ROI of the object. For the target that is an area, the purpose of determining the target position of the target is to determine 3D coordinates of at least two spots of the target.

The rotation angle of the first scanning location and the rotation angle of the second scanning location may be different or the same under a condition that the target is an area. If the rotation angle of the first scanning location and the rotation angle of the second scanning location are the same, the spatial location of the first scanning location and the spatial location of the second scanning location may be different.

In some embodiments, if the rotation angle of the first scanning location and the rotation angle of the second scanning location are the same, the spatial location of the first scanning location and the spatial location of the second scanning location may be two different locations on the center line of the X-rays emitted from the X-ray source 30 (as shown in FIG. 22A). In FIG. 22A, the purpose of determining the target position of the target is to determine 3D coordinates of $R_1$ and $R_2$. A segment $R_1R_2$ may be vertical to the center line (e.g., $A_4B_4$ or $A_5B_5$) of the X-rays emitted from the X-ray source 30. As shown in FIG. 22A, $A_4$ and $A_5$ may indicate scanning locations of the X-ray source 30. $C_4$ may refer to a location of $R_1$ in the first image. $D_4$ may indicate the location of $R_2$ in the first image. $C_5$ may indicate the location of $R_1$ in the second image. $D_5$ may indicate the location of $R_2$ in the second image. $B_4$ may indicate the center of the first image. $B_5$ may indicate the center of the second image. In some embodiments, the second location determination unit 930 may determine the 3D coordinates of $R_1$ and $R_2$ based on the process illustrated in FIG. 19 and/or FIG. 20A. In some embodiments, the second location determination unit 930 may determine the 3D coordinates of $R_1$ and $R_2$ based on Equation (3), Equation (4), and Equation (5) below:

$$A_4H = A_4B_4 \frac{HR_2}{B_4D_4}, \qquad (3)$$

$$A_5H = A_5B_5 \frac{HR_2}{B_5D_5}, \qquad (4)$$

and $$A_4H = A_5H + A_4A_5. \qquad (5)$$

The second location determination unit 930 may determine $HR_2$ based on Equation (3), Equation (4), and Equation (5). The second location determination unit 930 may determine $HR_1$ using a method same as the method of determining $HR_2$. The second location determination unit 930 may determine the 3D coordinates of $R_1$ and $R_2$ based on $HR_1$ and $HR_2$.

In some embodiments, if the rotation angle of the first scanning location and the rotation angle of the second scanning location are different, the spatial location of the first scanning location and the spatial location of the second scanning location may be two different locations in a direction perpendicular to the center line of the X-rays emitted from the X-ray source 30 (as shown in FIG. 22B). In FIG. 22B, the purpose of determining the target position of the target is to determine 3D coordinates of $R_1$ and $R_2$. The segment $R_1R_2$ may be vertical to the center line (e.g., $A_4B_4$ or $A_5B_5$) of the X-rays emitted from the X-ray source 30. $H_4$ may indicate an orthographic projection of $R_1$ and $R_2$ onto $A_4B_4$. $H_5$ may indicate an orthographic projection of $R_1$ and $R_2$ onto $A_5B_5$. Because the segment of $R_1R_2$ is vertical to $A_4B_4$ and $A_5B_5$, the orthographic projection of $R_1$ onto $A_4B_4$ and the orthographic projection of $R_2$ onto $A_4B_4$ may be the same, and the orthographic projection of $R_1$ onto $A_5B_5$ and the orthographic projection of $R_2$ onto $A_5B_5$ may be the same. In some embodiments, the second location determination unit 930 may determine the 3D coordinates of $R_1$ and $R_2$ based on the process illustrated in FIG. 19 and/or FIG. 20A. In some embodiments, the second location determination unit 930 may determine the 3D coordinates of $R_1$ and $R_2$ based on Equation (6), Equation (7), Equation (8), and Equation (9) below:

$$H_5R_2 = B_4D_5 \frac{A_5H_5}{A_5B_5}, \qquad (6)$$

-continued $$H_4R_2 = B_4D_4\frac{A_4H_4}{A_4B_4}, \quad (7)$$

$$H_5R_2 = H_4R_2 + B_4B_5, \quad (8)$$

and $$A_5H_5 = A_4H_4. \quad (9)$$

The second location determination unit 930 may determine $A_5H_5$ (or $A_4H_4$) based on Equation (6), Equation (7), Equation (8), and Equation (9). The second location determination unit 930 may determine $H_5R_2$ based on $A_5H_5$ (or $A_4H_4$) and Equation (6). The second location determination unit 930 may determine $H_4R_2$ based on $A_5H_5$ (or $A_4H_4$) and Equation (7). The second location determination unit 930 may determine $HR_1$ using the same technique as the technique for determining $HR_2$. The second location determination unit 930 may determine the 3D coordinates of $R_2$ based on $H_4R_2$ and $H_5R_2$. The second location determination unit 930 may determine the 3D coordinates of $R_1$ based on a method same as the method of determining the 3D coordinates of $R_2$.

Figure 23:
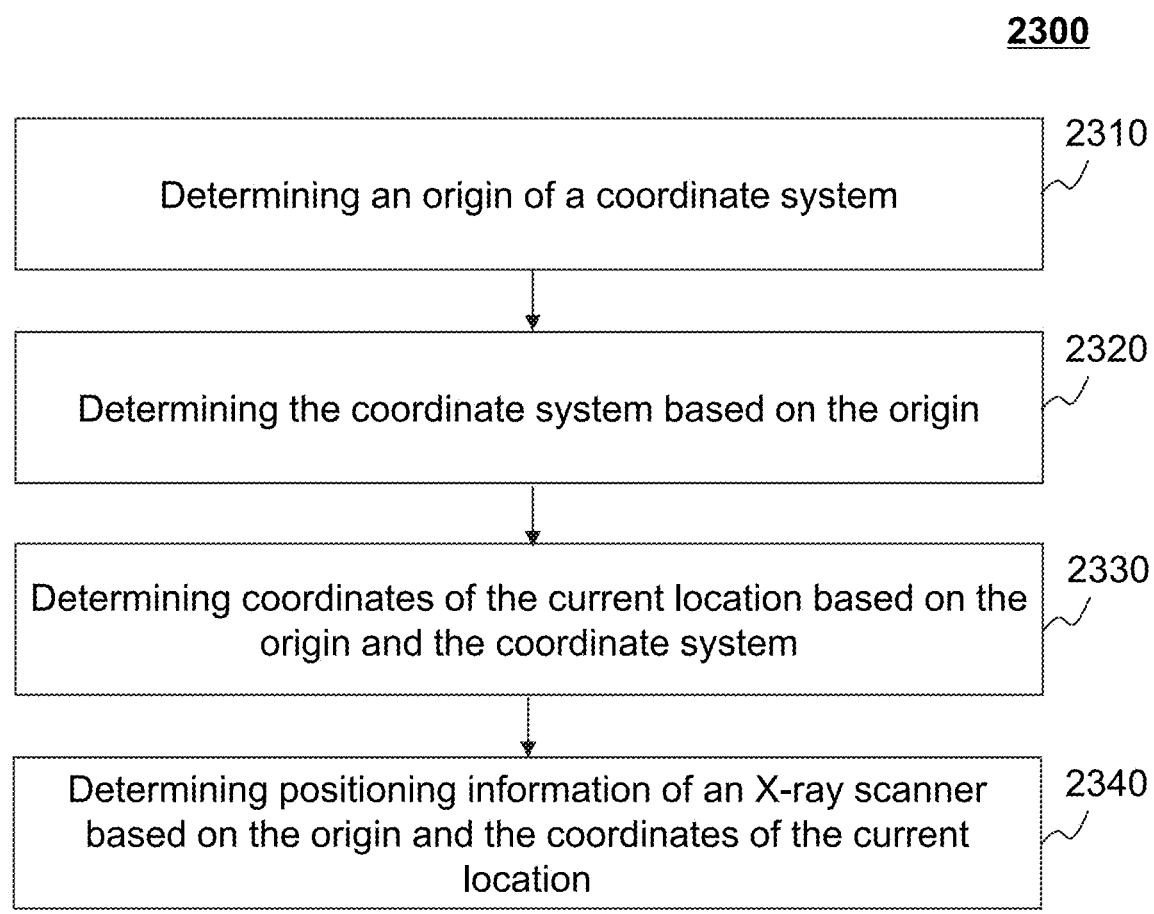
FIG. 23 is a flowchart illustrating an exemplary process for determining positioning information of an X-ray scanner according to some embodiments of the present disclosure.

FIG. 23 is a flowchart illustrating an exemplary process/method 2300 for determining positioning information of the X-ray scanner 110 according to some embodiments of the present disclosure. In some embodiments, the process/method 2300 may be implemented in the system 100 illustrated in FIG. 1. For example, the process/method 2300 may be stored in the storage device 150 and/or a storage apparatus (e.g., the storage 720, the storage 890, or the memory 860) in the form of instructions, and invoked and/or executed by the processing engine 140 (e.g., the processor 710 of the processing engine 140, one or more modules in the processing engine 140 illustrated in FIG. 9, or one or more units in the processing engine 140 illustrated in FIG. 9). The operations of the illustrated process/method presented below are intended to be illustrative. In some embodiments, the process/method 2300 may be accomplished with one or more additional operations not described, and/or without one or more of the operations discussed. Additionally, the order in which the operations of the process/method 2300 as illustrated in FIG. 23 and described below is not intended to be limiting.

In some embodiments, the processing engine 140 may perform the process/method 2300 to determine positioning information of the X-ray scanner 110. The positioning information of the X-ray scanner 110 may guide the X-ray scanner 110 to move from one location to another location.

In 2310, the origin determination unit 950 may determine an origin of a coordinate system. In some embodiments, after the X-ray scanner 110 scans an object at a first location, the X-ray scanner 110 may be moved away to a second location. Subsequently, the X-ray scanner 110 may be moved back to the first location to scan the object again. The origin determination unit 950 may designate the first location as the origin. In some embodiments, when the X-ray scanner 110 scans the object at the first location, the user may send instructions to make the origin determination unit 950 determine the first location as the origin. In some embodiments, when the X-ray scanner 110 scans the object at the first location, the origin determination unit 950 may determine the first location as the origin automatically. In some embodiments, if the X-ray scanner 110 scans the object at two or more locations, the origin determination unit 950 may automatically determine the location that the quality of the image corresponding to is most satisfactory among the several locations as the origin.

In 2320, the coordinate system determination unit 960 may determine a coordinate system based on the origin. The coordinate system may be a 2D coordinate system or a 3D coordinate system. In some embodiments, for a portable X-ray scanner, the coordinate system determination unit 960 may determine the coordinate system based on the ground. For example, the coordinate system determination unit 960 may determine a 2D coordinate system of which the X axis and the Y axis are on the ground. In some embodiments, for a suspension X-ray scanner, the coordinate system determination unit 960 may determine the coordinate system based on the ceiling. For example, the coordinate system determination unit 960 may determine a 2D coordinate system of which the X axis and the Y axis are on the ceiling.

In 2330, the current location determination unit 970 may determine coordinates of a current location of the X-ray scanner 110 based on the origin and the coordinate system. In some embodiments, the X-ray scanner 110 may be moved from the origin to the current location. Sensors mounted on the X-ray scanner 110 may determine a displacement from the origin to the current location. The current location determination unit 970 may determine the coordinates of the current location of the X-ray scanner 110 based on the displacement. Alternatively or additionally, the coordinates of the current location may be determined by a positioning technology in the X-ray scanner 110. The X-ray scanner 110 may transmit the coordinates of the current location to the current location determination unit 970.

In 2340, the positioning unit 940 may determine positioning information of the X-ray scanner 110 to be positioned at the origin from the current location of the X-ray scanner 110. The positioning information of the X-ray scanner 110 may include a translation distance along the X-axis direction of the coordinate system from the current location of the target to the origin, a translation distance along the Y-axis direction of the coordinate system from the current location of the target to the origin, a distance from the current location of the target to the origin, an angle between a line from the current location of the target to the origin and the X-axis (or Y-axis) direction of the coordinate system, a movement speed, a movement acceleration, a movement time, etc. In some embodiments, the processing engine 140 may display the positioning information of the X-ray scanner 110 on a screen. The processing engine 140 may display the positioning information of the X-ray scanner 110 in the form of text, picture, video, voice, etc. For example, the processing engine 140 may provide a route for moving the X-ray scanner 110 from the current location of the origin. As another example, the processing engine 140 may provide a notification by way of, for example, flashing a green icon when the X-ray scanner 110 arrives at the origin. As still another example, the processing engine 140 may use a sound to inform the user that the X-ray scanner 110 arrives at the origin. In some embodiments, the X-ray scanner 110 may be moved manually or automatically.

In some embodiments, the second positioning module 902 may determine any point as the origin and determine a coordinate system based on the origin. The second positioning module 902 may determine coordinates of the location that the user desires to move back to and coordinates of the current location of the X-ray scanner 110 based on the coordinate system. The second positioning module 902 may determine the positioning information of the X-ray scanner 110 based on the coordinates of the location that the user desires to move back to and the coordinates of the current location of the X-ray scanner 110.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, for example, an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed object matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. An X-ray scanner, comprising:
an X-ray source, a detector, an actuator and an indicator;
the X-ray source configured to emit X-rays;
the detector configured to detect the X-rays that are emitted from the X-ray source, wherein the detector and the X-ray source are spaced apart by a space;
the actuator configured to actuate the indicator based on a target in an X-ray image of an object imaged by the X-ray source and the detector, wherein the indicator indicates a target position on a surface of the object corresponding to the target.

2. The X-ray scanner of claim 1, further comprising a support having a first end and a second end, wherein the X-ray source is connected with the first end of the support, and the detector is connected with the second end of the support.

3. The X-ray scanner of claim 1, wherein the actuator is further configured to actuate the indicator to perform a translation, a swing, or a combination thereof according to positioning information of the indicator determined based on the X-ray image of the object, and the actuator is connected with the indicator.

4. The X-ray scanner of claim 1, wherein the indicator is located on a periphery of the space and connected with the detector.

5. The X-ray scanner of claim 4, wherein the indicator includes a first linear laser light and a second linear laser light.

6. The X-ray scanner of claim 5, wherein the detector includes a frame having a first side and a second side connected with the first side, the first linear laser light is connected with the first side of the frame, and the second linear laser light is connected with the second side of the frame.

7. The X-ray scanner of claim 6, wherein the first linear laser light emits first laser rays, the second linear laser light emits second laser rays, the first linear laser light and the second linear laser light are positioned such that the first laser rays and the second laser rays form an intersection indicating the target position.

8. The X-ray scanner of claim 6, wherein the indicator further includes a third linear laser light and a fourth linear laser light, the third linear laser light is connected with the first side of the frame, and the fourth linear laser light is connected with the second side of the frame.

9. The X-ray scanner of claim 8, wherein the frame further has a third side parallel to the first side and a fourth side parallel to the second side, the third linear laser light is connected with the third side of the frame, and the fourth linear laser light is connected with the fourth side of the frame.

10. The X-ray scanner of claim 8, wherein the first linear laser light emits first laser rays, the second linear laser light emits second laser rays, the third linear laser light emits third laser rays, the fourth linear laser light emits fourth laser rays, the first linear laser light, the second linear laser light, the third linear laser light, and the fourth linear laser light are positioned such that the first laser rays, the second laser rays, the third laser rays, and the fourth laser rays define an area indicating the target position.

11. The X-ray scanner of claim 5, wherein the actuator includes a first actuating unit and a second actuating unit, the first actuating unit is configured to actuate the first linear laser light, and the second actuating unit is configured to actuate the second linear laser light.

12. The X-ray scanner of claim 11, wherein the first actuating unit includes a first transmission, the first transmission includes at least one of a gear transmission, a chain transmission, or a belt transmission, and the first linear laser light is connected with the first transmission.

13. The X-ray scanner of claim 12, wherein the first linear laser light is connected with the first transmission through a first translation board.

14. The X-ray scanner of claim 4, wherein the indicator includes a fifth laser light, the fifth laser light is a point laser light or a cross laser light, and the fifth laser light is adjustable by the translation or the swing such that the fifth laser light indicates the target position.

15. The X-ray scanner of claim 14, wherein the actuator includes a third actuating unit and a fourth actuating unit, the third actuating unit is configured to actuate the fifth laser light to perform the translation, and the fourth actuating unit is configured to actuate the fifth laser light to perform the swing.

16. The X-ray scanner of claim 15, wherein the third actuating unit includes a second transmission and a second translation board, and the second translation board is connected with the second transmission.

17. The X-ray scanner of claim 16, wherein the fourth actuating unit includes a third transmission and a rotation board, the third transmission includes a gear transmission and an electric motor, the fifth laser light is connected with the gear transmission, the gear transmission is connected with a first side of the rotation board, the electric motor is connected with a second side of the rotation board that is opposite to the first side of the rotation board, and the rotation board is connected with the second translation board.

18. The X-ray scanner of claim 17, wherein the gear transmission includes a driving gear and a driven gear, and the fifth laser light is connected with the driven gear.

19. The X-ray scanner of claim 18, wherein the driving gear is connected with the rotation board through an axis and is rotatable around the axis, the driven gear is connected with the rotation board through a locating pin inserted in an opening on the driven gear such that the fifth laser light is rotatable along the opening.

20. The X-ray scanner of claim 1, further comprising:
a rangefinder configured to determine a distance between the target position and the detector.

* * * * *